United States Patent
Gak et al.

(10) Patent No.: US 9,062,334 B2
(45) Date of Patent: Jun. 23, 2015

(54) **METHOD FOR PRODUCING PYRROLOQUINOLINE QUINONE USING A BACTERIUM OF THE GENUS *METHYLOBACTERIUM* OR *HYPHOMICROBIUM***

(71) Applicant: AJINOMOTO CO., INC., Tokyo (JP)

(72) Inventors: Evgeniy Rodionovich Gak, Moscow (RU); Natalya Vasilievna Gorshkova, Moscow (RU); Irina L'vovna Tokmakova, Moscow region (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/010,101

(22) Filed: Aug. 26, 2013

(65) Prior Publication Data

US 2013/0337511 A1    Dec. 19, 2013

Related U.S. Application Data

(63) Continuation of application No. PCT/JP2012/055727, filed on Feb. 28, 2012.

(30) Foreign Application Priority Data

Mar. 3, 2011    (RU) ................................ 2011108196

(51) Int. Cl.
*C12P 17/18*    (2006.01)
*C07K 14/195*    (2006.01)

(52) U.S. Cl.
CPC .............. *C12P 17/182* (2013.01); *C07K 14/195* (2013.01)

(58) Field of Classification Search
CPC ...... C07K 14/195; C12P 17/18; C12P 17/182
USPC .......................................................... 435/119
See application file for complete search history.

(56) References Cited

FOREIGN PATENT DOCUMENTS

| CN | 102146123 | 8/2011 |
|---|---|---|
| CN | 102219836 | 10/2011 |
| EP | 0206471 B1 | 12/1986 |
| WO | WO2012/118225 | 9/2012 |

OTHER PUBLICATIONS

Database WPI, Week 201173, XP-002676178, AN: 2011-L10954, & CN102146123A.
Database WPI, Week 201109, XP-002676179, AN: 2011-0P34142, & CN102219836A.
Duine, J.A., et al., "The role of PQQ and quinoproteins in methylotrophic bacteria," FEMS Microbiol. Rev. 1990;87:221-226.
Goodwin, P. M., et al., "The Biochemistry, Physiology and Genetics of PQQ and PQQ-containing Enzymes," Advances in Microbial Physiology, vol. 40, pp. 1-80, 1998.
Hoelscher, T., et al., "Knockout and Overexpression of Pyrroloquinoline Quinone Biosynthetic Genes in *Gluconobacter oxydans* 621H," J. Bacteriol. 2006;188(21):7668-7676.
Meulenberg, J. J. M., et al., "Cloning of *Klebsiella pneumoniae* pqq genes and PQQ biosynthesis in *Escherichia coli*," FEMS Microbiol. Lett. 1990;71:337-344.
Houck, D. R., et al., "PQQ: Biosynthetic Studies in *Methylobacterium* AM1 and *Hyphomicrobium* X Using Specific 13C Labeling and NMR," Antonie van Leeuwenhoek 1989;56(1):93-101.
Toyama, H., et al., "pqqA is not required for biosynthesis of pyrroloquinoline quinone in *Methylbacterium extorquens* AM1," Microbiol. 1998;144:183-191.
Toyama, H., et al., "Sequence analysis of pqq genes required for biosynthesis of pyrroloquinoline quinone in *Methylbacterium extorquens* AM1 and the purification of a biosynthetic intermediate," Microbiol. 1997;143:595-602.
Urakami, T., et al., "Production of Pyrroloquinoline Quinone by Using Methanol-Utilizing Bacteria," Appl. Environmen. Microbiol. 1992;58(12):3970-3976.
Yang, X.-P., et al., "Pyrroloquinoline quinone biosynthesis in *Escherichia coli* through expression of the *Gluconobacter oxydans* pqqABCDE gene cluster," J. Ind. Microbiol. Biotechnol. 2010;37:575-580.
International Search Report for PCT Patent App. No. PCT/JP2012/055727 (Jun. 6, 2012).
Goosen, N., et al., "*Acinetobacter calcoaceticus* genes involved in biosynthesis of the coenzyme pyrrolo-quinoline-quinone: nucleotide sequence and expression in *Escherichia coli* K-12," J. Bacteriol. 1989;171(1):447-455.
Puehringer, S., et al., "The pyrroloquinoline quinone biosynthesis pathway revisited: A structural approach," BMC Biochem. 2008;9(8);doi:10.1186/1471-2091-9-8.
Velterop, J. S., et al., "Synthesis of pyrroloquinoline quinone in vivo and in vitro and detection of an intermediate in the biosynthetic pathway," J. Bacteriol. 1995;177(17):5088-5098.
Wecksler, S. R., et al., "Interaction of PqqE and PqqD in the pyrroloquinoline quinone (PQQ) biosynthetic pathway links PqqD to the radical SAM superfamily," Chem. Commun. 2010;46:7031-7033.
International Preliminary Report on Patentability for PCT Patent App. No. PCT/ JP2012/055727 (Sep. 12, 2013).
Toyama, H., et al., "Sequence analysis of pqq genes required for biosynthesis of pyrroloquinoline quinone in *Methylobacterium extorquens* AM1 and the purification of a biosynthetic intermediate," Microbiol. 1997;143:595-602.
Hölscher, T., et al., "Knockout and Overexpression of Pyrroloquinoline Quinone Biosynthetic Genes in *Gluconobacter oxydans* 621H," J. Bacteriol. 2006;188(21):7668-7676.

*Primary Examiner* — Karen Cochrane Carlson
(74) *Attorney, Agent, or Firm* — Shelly Guest Cermak; Cermak Nakajima & McGowan LLP

(57) ABSTRACT

The present invention provides a method for producing PQQ using a bacterium belonging to the genera *Methylobacterium* or *Hyphomicrobium*, which has been modified to enhance the expression of pqq gene cluster and/or gene(s) encoding a precursor for PQQ biosynthesis.

12 Claims, 10 Drawing Sheets

Fig. 2

```
Q488A4      ----------------------------------------MWTKPKFEEMRLGFEVTLYISNR
D4IFL0      ----------------------------------------MQWTKPTFIDMRLGLEVTLYISNR
Q4KEK3      ----------------------------------------MWHKPAYTDLRIGFEVTMYFANR
Q4K4V2      ----------------------------------------MTWSKPAYTDLRIGFEVTMYFASR
D8JSB5      ------------------MQESLLK---------EPEAKTWVAPAYCDLRLGFEVTAYIYVR
B2UEV0      ----------------------------------------MAWQKPEATDLRFGFEITMYIANR
B1Y7S1      MVLAMTPRAPAPTLHPHQHTLLASLTRTANPIEGDLMTWTTPAACDFRFGFEITMYIAAR
B2U9I4      ----------------------------------------MNWTTPAYTELRLGFEITMYIANR
Q608P4      ----------------------------------------MRWEKPSYNDMRFGFEVTMYIYNR
C6WTX0      ----------------------------------------MWTTPAATEMRFGFEVTMYVMNK
D7DHP0      ----------------------------------------MWTTPAATEMRFGFEVTMYVMNK
Q1GX88      --------MSKLGLYDGNHGLRGTDCAASTHLKRRLIMWTKPEVTEMRFGFEVTMYVCNR
Q49148      ----------------------------------------MK-WAAPIVSEICVGMEVTSYESAE
C7C9M1      ----------------------------------------MK-WAAPIVSEICVGMEVTSYESAE
B1LV85      ----------------------------------------MK-WAAPIVSEICVGMEVTSYESAE
C5AQY4      ----------------------------------------MK-WSAPIVAEICVGMEVTSYESAE
C7CLK2      ----------------------------------------MK-WSAPIVAEICVGMEVTSYESAE
C5AQY5      ----------------------------------------MK-WSAPVVAEICVGMEVTSYESAE
D8JXU1      -----------------------------MESSYRFGGTTMKIWTKPAVREQEVGLEVTSYLPAE
D8JQF5      ---------------------------MED-------IMKTWTKPAVREQEVGLEVTSYLPAE
A4YZY3      ----------------------------------------MA-WKAPKIVEVPVGMEINMYACAA
A4YZ28      ----------------------------------------MA-WKTPKIVEVPVGMEINMYACAA
A4YNW1      ----------------------------------------MS-WTAPKIVEVPVGMEINMYACAS
Q9L3B4      ----------------------------------------MA-WNTPKVTEIPLGAEINSYVCGE
A8LN54      ----------------------------------------MA-WTKPIIREIECGMEINMYGPDS
                                                    *    *   :   * *:. *

Q488A4      --------
D4IFL0      --------
Q4KEK3      --------
Q4K4V2      --------
D8JSB5      --------
B2UEV0      --------
B1Y7S1      --------
B2U9I4      --------
Q608P4      --------
C6WTX0      --------
D7DHP0      --------
Q1GX88      --------
Q49148      IDTFN---
C7C9M1      IDTFN---
B1LV85      IDTFN---
C5AQY4      IDTFN---
C7CLK2      IDTFN---
C5AQY5      IDTFN---
D8JXU1      IDLI----
D8JQF5      IDLI----
A4YZY3      RK------
A4YZ28      RK------
A4YNW1      RKAERRS-
Q9L3B4      KK------
A8LN54      DEEREVLF
```

METHOD FOR PRODUCING PYRROLOQUINOLINE QUINONE USING A BACTERIUM OF THE GENUS *METHYLOBACTERIUM* OR *HYPHOMICROBIUM*

This application is a Continuation of, and claims priority under 35 U.S.C. §120 to, International Application No. PCT/JP2012/055727, filed Feb. 28, 2012, and claims priority therethrough under 35 U.S.C. §119 to Russian Patent Application No. 2011108196, filed Mar. 3, 2011, the entireties of which are incorporated by reference herein. Also, the Sequence Listing filed electronically herewith is hereby incorporated by reference (File name: 2013-08-26_US-460 Seq List; File size: 68 KB; Date recorded: Aug. 26, 2013).

BACKGROUND OF THE INVENTION

1. Field of the Invention

The present invention relates to the microbiological industry, and specifically to a method for producing pyrroloquinoline quinine (PQQ) using a bacterium of the genus *Methylobacterium* or *Hyphomicrobium* which has been modified to enhance the expression of the pqq gene cluster and/or gene(s) encoding a precursor for PQQ biosynthesis.

2. Brief Description of the Related Art

Pyrroloquinoline quinine (PQQ) is the cofactor for several bacterial dehydrogenases including glucose dehydrogenase and methanol dehydrogenase located in the periplasm of Gram-negative bacteria and may be accumulated extracellularly by cultivating these bacteria. All of the PQQ-producing strains have PQQ-dependent quinoproteins.

A method for the preparation of PQQ using bacteria belonging to the genera *Achromobacter, Methylobacillus, Methylomonas, Methanomonas, Protaminobacter, Methylobacterium, Protomonas, Mycoplana, Ancyclobacter, Microcyclus, Hyphomicrobium, Xanthobacter, Thiobacillus, Alteromonas, Methylophaga* and some species of the genus *Pseudomonas*, which are cultivated in a medium containing methanol and/or methylamine as a carbon source, is disclosed (EP0206471 B1).

Genes involved in PQQ biosynthesis have been characterized for several bacteria, including *Klebsiella pneumoniae, Acinetobacter calcoaceticus, Methylobacterium extorquens*, and *Gluconobacter oxydans*. Six genes and seven genes are required in *K. pneumoniae* and *M. extorquens* (AM1), respectively, and only four genes are required in *A. calcoaceticus* for PQQ biosynthesis. The pqqA genes from different species encode small peptides of 23 to 29 amino acids which contain conserved glutamic acid and tyrosine residues. PQQ is derived from the two amino acids glutammic acid and tyrosine encoded in the precursor peptide PqqA. Presumably, five reactions are necessary to form PQQ (Puehringer et al. BMC Biochemistry 2008, 9:8 doi:10.1186/1471-2091-9-8). Some of the proteins involved in PQQ biosynthesis have been functionally characterized.

The PqqB protein is supposed to be involved in transport of PQQ into the periplasm. It has been reported that a knock out of PqqB produces small amounts of PQQ in the cytosol and that no PQQ is secreted into the periplasm (Velterop et al. Journal of bacteriology (1995) 177(17):5088-5098). The PqqC protein is an oxidase which catalyzes the final step in PQQ formation. The functions of PqqD protein are still unknown. Recently, the interaction of PqqD protein with the radical SAM enzyme PqqE has been demonstrated in *K. pneumoniae* (Wecksler S R et al. Chem Commun 2010 Oct. 7; 46(37):7031-3).

Based on sequence analysis and homology models, it is supposed that PqqE recognizes the PqqA protein and forms a bond between the C atoms from the glutammic acid and tyrosine in PqqA, and, therefore, enables recognition of the modified PqqA by PqqF protein. In the next stage, PqqF is suggested to catalyze cutting of the generated glutammic acid-tyrosine pair out of PqqA protein (Puehringer et al. BMC Biochemistry 2008, 9:8 doi:10.1186/1471-2091-9-8).

It was revealed that PQQ biosynthesis in *Escherichia coli*, which does not possess an ability to produce PQQ, can be achieved through the expression of pqq gene clusters of *A. calcoaceticus* (Goosen N. et al. J Bacteriol (1989) 171:447-455), *K. pneumoniae* (Meulenberg J J M et al. FEMS Microbiol Lett (1990) 71:337-344), and *G. oxydans* (Yang et al. Journal of Industrial Microbiology&Biotechnology (2010), 37(6), 575-580). Also, the positive effect of copies of some pqq genes on PQQ production in *Methylobacterium extorquens* AM1 was described (Wu, Bo; Zhao, Yong-fang; Wang, Yin-shan.Wuhan Daxue Xuebao, Ziran Kexueban (1999) 45(6), 869-872). Deletion of mxbM gene and pqqABC/DE gene cluster in *M. extorquens* AM1 led to absence of PQQ production. The deletion mutant transformed by a plasmid harboring mxbM gene and pqqABC/DE gene cluster produced PQQ in larger amounts than the wild-type, presumably as a result of the higher copy number of pqq genes. (Toyama H. and Lidstorm M E. Microbiology (1998), 144, 183-191).

But, currently, there have been no reports of enhancing expression of the pqq gene cluster in a bacterium, belonging to the genus *Hyphomicrobium*, and enhancing expression of the additional pqqA gene(s) encoding a precursor for PQQ biosynthesis in a bacterium of the genera *Methylobacterium* or *Hyphomicrobium* for the purpose of producing PQQ.

SUMMARY OF THE INVENTION

Aspects of the present invention include providing methods for producing PQQ using a bacterium belonging to the genera *Methylobacterium* or *Hyphomicrobium*.

The above aspects were achieved by finding that enhancing expression of the pqq gene cluster and gene(s) encoding PqqA homologous proteins can enhance production of PQQ.

It is an aspect of the present invention to provide a method for producing PQQ comprising cultivating a bacterium belonging to the genus *Hyphomicrobium*, and collecting PQQ from the culture medium, wherein the bacterium has been modified to enhance expression of pqq gene cluster.

It is a further aspect of the present invention to provide the method as described above, wherein said pqq gene cluster is the pqqABC/DE operon from *Methylobacterium extorquens*.

It is a further aspect of the present invention to provide the method as described above, wherein said pqqABC/DE operon comprises DNA fragments of SEQ ID NO: 1, SEQ ID NO: 3, SEQ ID NO: 5, and SEQ ID NO: 7, or variants thereof.

It is a further aspect of the present invention to provide the method as described above, wherein said pqq gene cluster is the pqqABCDE cluster from *Hyphomicrobium denitrificans*.

It is a further aspect of the present invention to provide the method as described above, wherein said pqqABCDE cluster comprises DNA fragments of SEQ ID NO: 14, SEQ ID NO: 16, SEQ ID NO: 18, SEQ ID NO: 20, and SEQ ID NO: 22, or variants thereof.

It is a further aspect of the present invention to provide the method as described above, wherein the expression of said gene cluster is enhanced by increasing said gene cluster copy number.

It is a further aspect of the present invention to provide the method as described above, wherein the increasing said gene cluster copy number is achieved by introducing into the bacterium a vector containing said gene cluster.

It is a further aspect of the present invention to provide the method as described above, wherein said bacterium is *Hyphomicrobium denitrificans*.

It is a further aspect of the present invention to provide the method as described above, wherein said culture medium contains methanol as a carbon source.

It is an aspect of the present invention to provide a method for producing PQQ comprising cultivating a bacterium belonging to the genera *Methylobacterium* or *Hyphomicrobium*, having enhanced expression of pqq gene cluster, and collecting PQQ from the culture medium, wherein said bacterium has been further modified to enhance expression pqqA-like gene(s).

It is a further aspect of the present invention to provide the method as described above, wherein said pqq gene cluster is the pqqABC/DE operon from *Methylobacterium extorquens*.

It is a further aspect of the present invention to provide the method as described above, wherein said pqqABC/DE operon comprises DNA fragments of SEQ ID NO: 1, SEQ ID NO: 3, SEQ ID NO: 5, and SEQ ID NO: 7, or variants thereof.

It is a further aspect of the present invention to provide the method as described above, wherein said pqq gene cluster is the pqqABCDE cluster from *Hyphomicrobium denitrificans*.

It is a further aspect of the present invention to provide the method as described above, wherein said pqqABCDE cluster comprises DNA fragments of SEQ ID NO: 14, SEQ ID NO: 16, SEQ ID NO: 18, SEQ ID NO: 20, and SEQ ID NO: 22, or variants thereof.

It is a further aspect of the present invention to provide the method as described above, wherein said pqqA-like gene is selected from the group consisting of:

- a DNA fragment that encodes a protein comprising the amino acid sequence of SEQ ID NO: 2;
- a DNA fragment that encodes a protein comprising the amino acid sequence SEQ ID NO: 2, but that contains substitutions, deletions, insertions, additions or inversions of one or several amino acid residues, and said protein has the function of a PQQ precursor;
- a DNA fragment that encodes a protein comprising the amino acid sequence of SEQ ID NO: 11;
- a DNA fragment that encodes a protein comprising the amino acid sequence of SEQ ID NO: 11, but that contains substitutions, deletions, insertions, additions or inversions of one or several amino acid residues, and having the function of a PQQ precursor;
- a DNA fragment that encodes a protein comprising the amino acid sequence of SEQ ID NO:13;
- a DNA fragment that encodes a protein comprising the amino acid sequence of SEQ ID NO: 13, but that contains substitutions, deletions, insertions, additions or inversions of one or several amino acid residues, and said protein has the function of a PQQ precursor;
- a DNA fragment that encodes a protein comprising the amino acid sequence of SEQ ID NO: 15;
- a DNA fragment that encodes a protein comprising the amino acid sequence of SEQ ID NO: 15, but that contains substitutions, deletions, insertions, additions or inversions of one or several amino acid residues, and said protein has the function of a PQQ precursor;
- a DNA fragment that encodes a protein comprising the amino acid sequence of SEQ ID NO: 26;
- a DNA fragment that encodes a protein comprising the amino acid sequence of SEQ ID NO: 26, but that contains substitutions, deletions, insertions, additions or inversions of one or several amino acid residues, and said protein has the function of a PQQ precursor;
- a DNA fragment that encodes a protein comprising the amino acid sequence of SEQ ID NO: 28;
- a DNA fragment that encodes a protein comprising the amino acid sequence of SEQ ID NO: 28, but that contains substitutions, deletions, insertions, additions or inversions of one or several amino acid residues, and said protein has the function of a PQQ precursor; and
- combinations thereof.

It is a further aspect of the present invention to provide the method as described above, wherein the expression of said gene cluster or gene(s) is/are enhanced by increasing said gene cluster or gene(s) copy number.

It is a further aspect of the present invention to provide the method as described above, wherein the increasing said gene cluster or gene(s) copy number is/are achieved by introducing into the bacterium a vector containing said gene cluster or gene(s) copy number.

It is a further aspect of the present invention to provide the method as described above, wherein said bacterium is *Hyphomicrobium denitrificans*.

It is a further aspect of the present invention to provide the method as described above, wherein said bacterium is *Methylobacterium extorquens*.

It is a further aspect of the present invention to provide the method as described above, wherein said culture medium comprises methanol as a carbon source.

BRIEF DESCRIPTION OF THE DRAWINGS

FIG. 2 shows an alignment of the PqqA homologous proteins from various microorganisms.

Q49148—encoded by pqqA gene from *Methylobacterium extorquens* AM1 (SEQ ID No: 2)
C5AQY4—encoded by pqqA2 gene from *Methylobacterium extorquens* AM1 (SEQ ID No: 11)
C5AQY5—encoded by pqqA3 gene from *Methylobacterium extorquens* AM1 (SEQ ID No: 13)
C7C9M1—encoded by gene locus from *Methylobacterium extorquens* DM4 (SEQ ID No: 2)
C7CLK2—encoded by gene locus from *Methylobacterium extorquens* DM4 (SEQ ID No: 11)
D8JXU1—encoded by pqqA gene from *Hyphomicrobium denitrificans* ATCC51888 (SEQ ID No: 15)
D8JSB5—encoded by pqqA2 gene from *Hyphomicrobium denitrificans* ATCC51888 (SEQ ID No: 26)
D8JQF5—encoded by pqqA3 gene from *Hyphomicrobium denitrificans* ATCC51888 (SEQ ID No: 28)
Q4KEK3—encoded by gene locus PFL_2223 (NCBI Entrez Gene) from *Pseudomonas fluorescens* Pf-5 (strain: Pf-5) (SEQ ID No: 37)
Q4K4V2—encoded by gene locus PFL_5673 (NCBI Entrez Gene) from *Pseudomonas fluorescens* Pf-5 (strain: Pf-5) (SEQ ID No: 38)
B2UEV0—encoded by gene locus Rpic_0286 (NCBI Entrez Gene) from *Ralstonia pickettii* 12J (SEQ ID No: 39)
B2U914—encoded by gene locus Rpic_2488 (NCBI Entrez Gene) from *Ralstonia pickettii* 12J (SEQ ID No: 40)
C6WTX0—encoded by gene loci Mmol_0459, Mmol_0021, Mmol_0993, or Mmol_0794 (NCBI Entrez Gene) from *Methylotenera mobilis* JLW8 (SEQ ID No: 41)

A4YZY3—encoded by gene locus BRAD05793 (NCBI Entrez Gene) from *Bradyrhizobium* sp. ORS278 (SEQ ID No: 42)

A4YZ28—encoded by gene locus BRAD05478 (NCBI Entrez Gene) from *Bradyrhizobium* sp. ORS278 (SEQ ID No: 43)

A4YNW1—encoded by gene locus BRADO1710 (NCBI Entrez Gene) from *Bradyrhizobium* sp. ORS278 (SEQ ID No: 44)

Q608P4—encoded by gene locus MCA1445.1 (NCBI Entrez Gene) from *Methylococcus capsulatus* Bath (SEQ ID No: 45)

Q488A4—encoded by gene locus CPS_0862 (NCBI Entrez Gene) from *Colwellia psychrerythraea* 34H (SEQ ID No: 46)

Q9L3B4—encoded by gene locus GOX0987 (NCBI Entrez Gene) from *Gluconobacter oxydans* 621H (SEQ ID No: 47)

Q1GX88—encoded by gene locus Mfla_0021 (NCBI Entrez Gene) from *Methylobacillus flagellatus* KT (SEQ ID No: 48)

A8LN54—encoded by gene locus Dshi_0450 (NCBI Entrez Gene) from *Dinoroseobacter shibae* DFL 12 (SEQ ID No: 49)

B1LV85—encoded by gene locus Mrad2831_0519 (NCBI Entrez Gene) from *Methylobacterium radiotolerans* JCM 2831 (SEQ ID No:2)

D41FL0—encoded by gene locus EAM_0512A(NCBI Entrez Gene) from *Erwinia amylovora* ATCC 49946 (SEQ ID No: 50)

D7DHP0—encoded by gene loci M301_0054, M301_2651, M301_1191, or M301_2123 (NCBI Entrez Gene) from *Methylotenera* sp. 301 (SEQ ID No: 41)

B1Y7S1—encoded by gene locus Lcho_0244 (NCBI Entrez Gene) from *Leptothrix cholodnii* (strain ATCC 51168, LMG 8142, SP-6) (*Leptothrix discophora* SP-6) (SEQ ID NO: 51)

Figure 3:
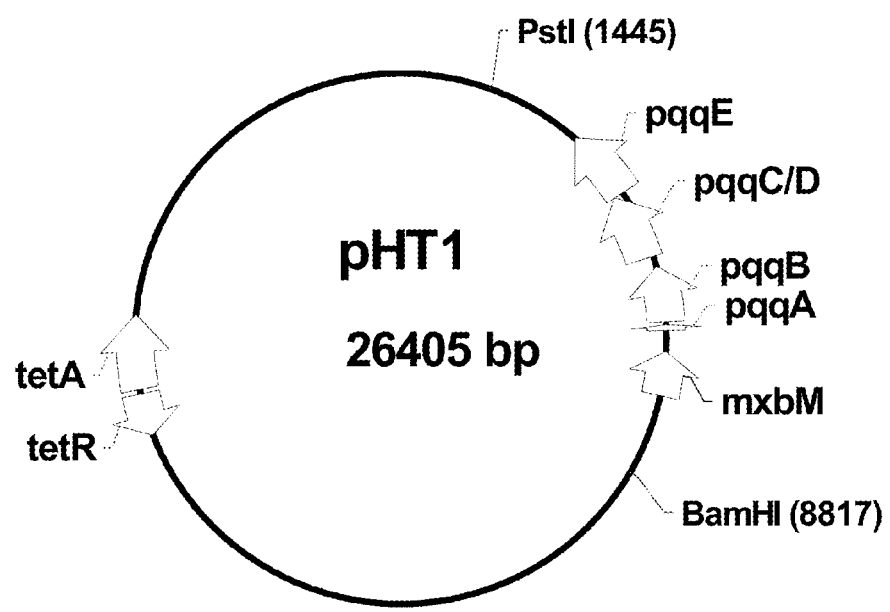

FIG. 3 shows a map of plasmid pHT1.

Figure 4:
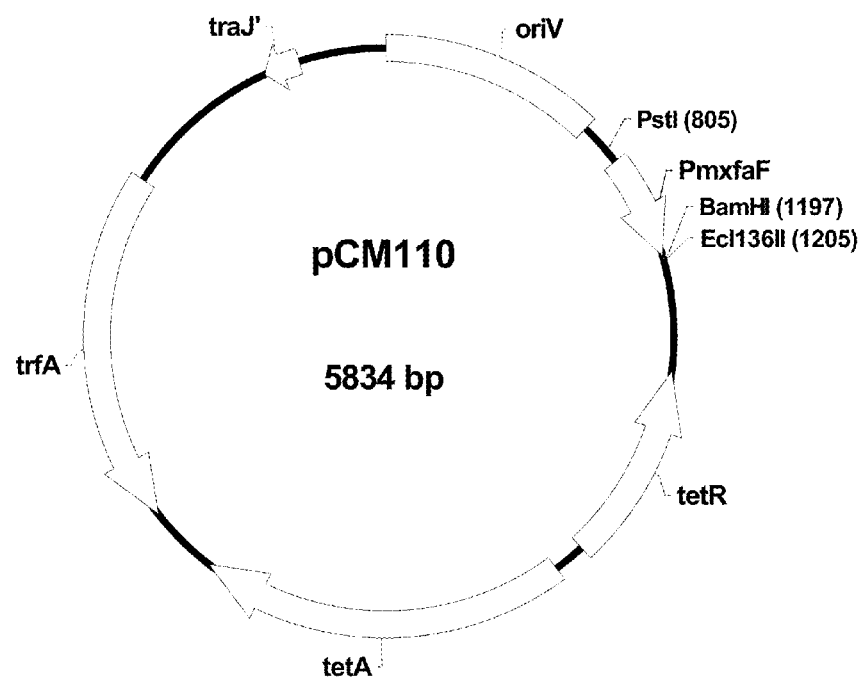

FIG. 4 shows a map of plasmid pCM110.

Figure 5:
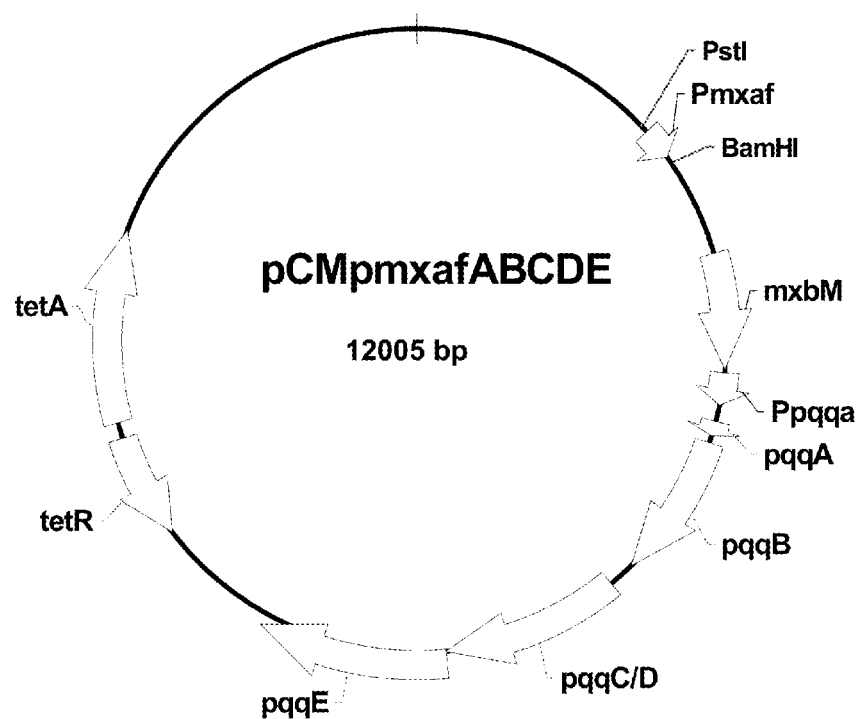

FIG. 5 shows a map of plasmid pPQQ1 (pCMp$_{maxaf}$AB-CDE).

Figure 6:
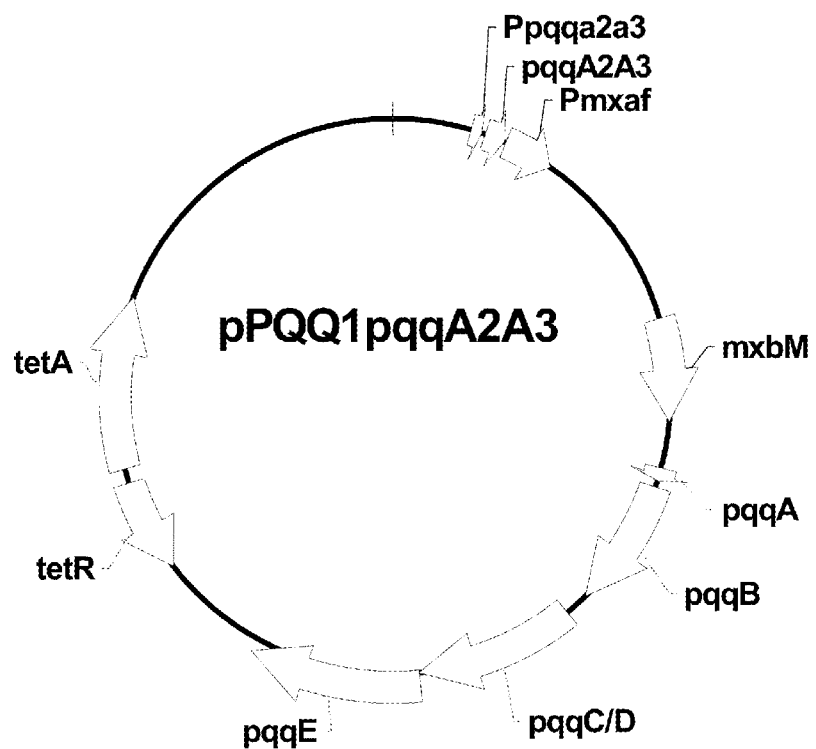

FIG. 6 shows a map of plasmid pPQQ1pqqA2A3.

Figure 7:
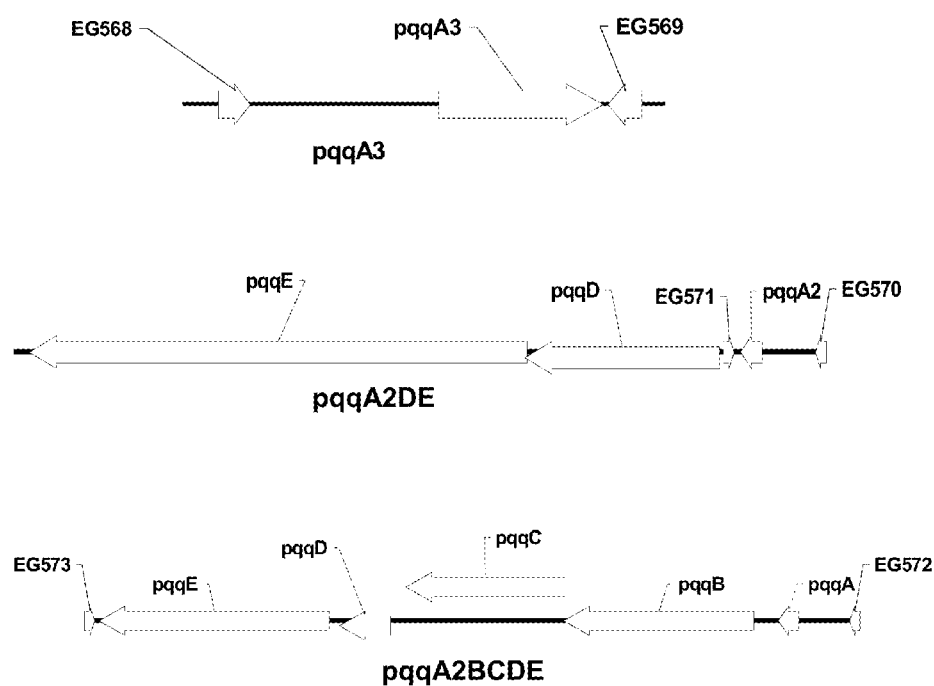

FIG. 7 shows genetic organization of the pqq genes on the *H. denitrificans* chromosome. The positions of the primers used for PCR-amplification are shown by the arrows.

Figure 8:
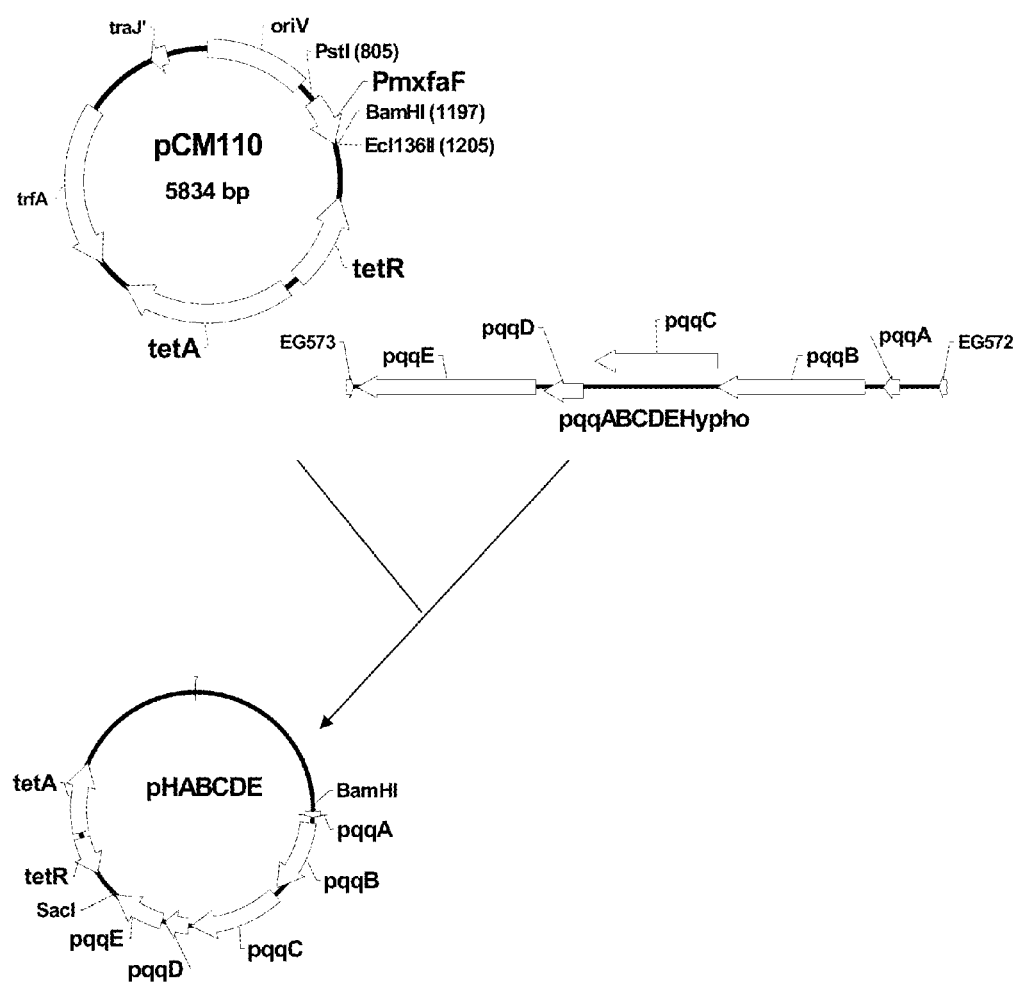

FIG. 8 shows construction of plasmid pHABCDE.

Figure 9:
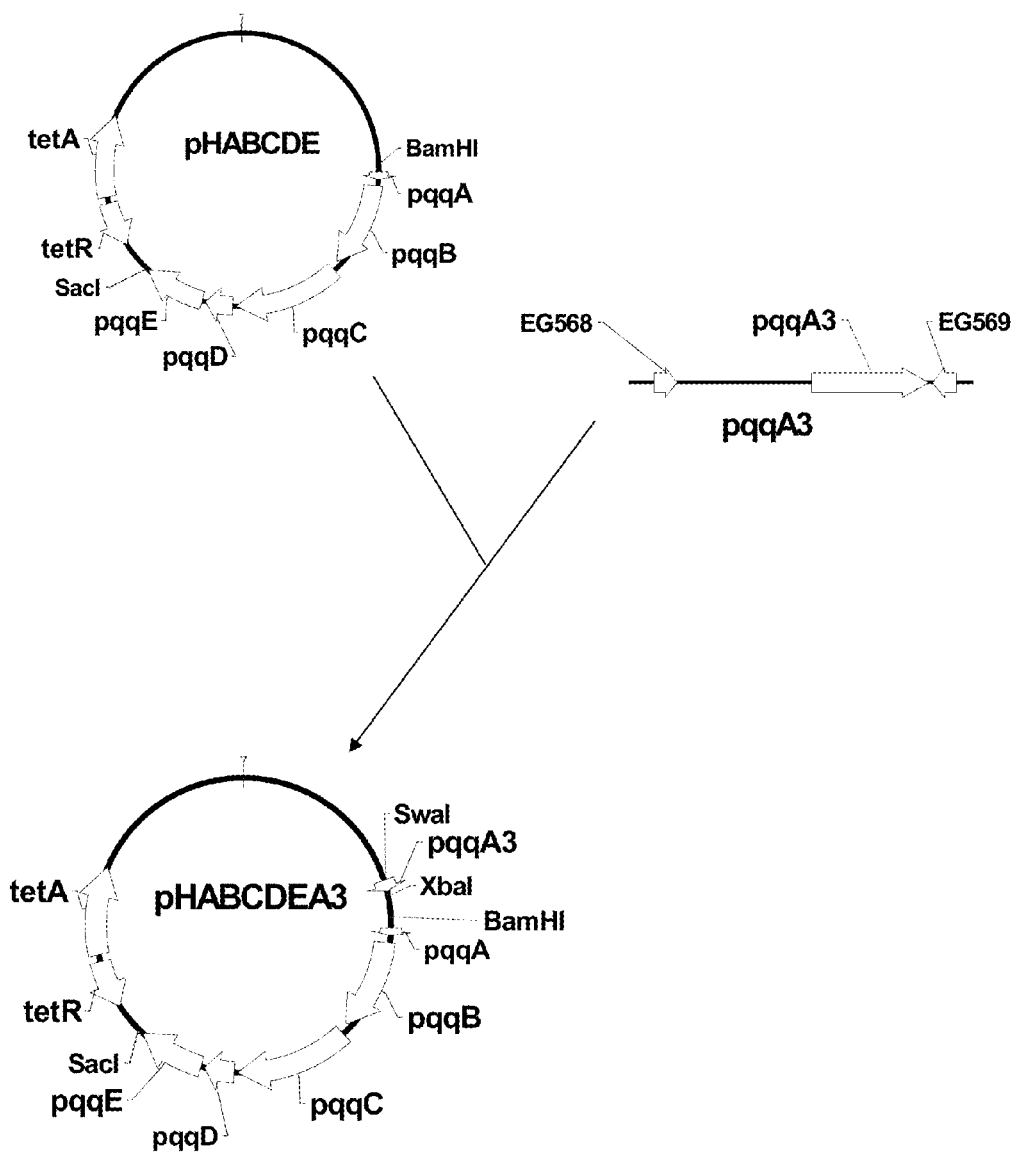

FIG. 9 shows construction of plasmid pHABCDEA3.

Figure 10:
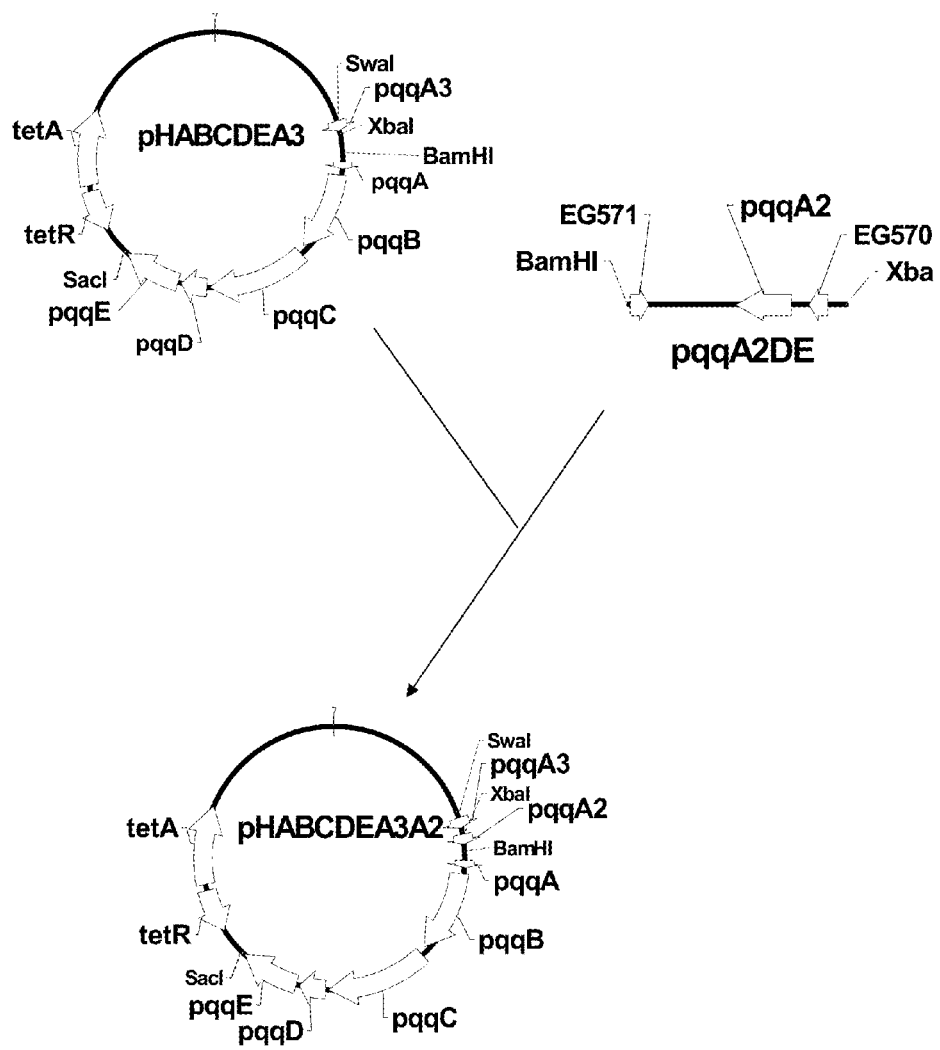

FIG. 10 shows construction of plasmid pHABCDEA3A2.

DESCRIPTION OF THE PREFERRED EMBODIMENTS

The present invention is described in detail below.

1. Bacterium

The bacterium according to the presently disclosed subject matter can be a PQQ-producing bacterium, wherein the bacterium has been modified to have enhanced expression of the genes involved in the pyrroloquinoline quinone biosynthesis.

The term "PQQ-producing bacterium" can mean a bacterium which has an ability to produce and excrete a PQQ into a medium, when the bacterium is cultured in the medium. The term "PQQ-producing bacterium" also can mean a bacterium which is able to produce and cause accumulation of PQQ in a culture medium in an amount larger than a wild-type or parental strain, for example, *Methylobacterium*, such as the *M. extorquens* strain AM1, or *Hyphomicrobium*, such as the *H. denitrificans* strain ATCC51888. The term "PQQ-producing bacterium" can also mean that the microorganism is able to cause accumulation in a medium of an amount not less than 0.3 mg/L, and in another example, not less than 1.0 mg/L, of PQQ.

The phrase "a bacterium belonging to the genus *Methylobacterium*" can mean that the bacterium is classified as the genus *Methylobacterium* according to the classification known to a person skilled in the art of microbiology. Specifically, those classified into the group *Methylobacterium* according to the taxonomy used by the NCBI (National Center for Biotechnology Information) database (www.ncbi.nlm.nih.gov/Taxonomy/Browser/wwwtax.cgi) can be used. Examples of the bacterium belonging to the genus *Methylobacterium* include, but are not limited to, *Methylobacterium extorquens* (*M. extorquens*), *Methylobacterium chloromethanicum*, *Methylobacterium mesophilicum*, *Methylobacterium nodulans*, *Methylobacterium organophilum*, *Methylobacterium oryzae*, *Methylobacterium podarium*, *Methylobacterium populi*, *Methylobacterium radiotolerans*, *Methylobacterium rhodesianum*, *Methylobacterium variabile*, *Methylobacterium* sp., etc. According to the present taxonomy of the genus, *Protomonas* is reclassified into the genus *Methylobacterium* (Bousfield I J and Green P N. Int J Syst Bacteriol 35 (1985), 209). The species *Pseudomonas rhodos*, *Pseudomonas radiora*, and *Pseudomonas mesophilica*, were also transferred to the genus *Methylobacterium* (Green P N and Bousfield I J. Int J Syst Bacteriol 33 (1983), 875-877).

The phrase "bacterium belonging to the genus *Hyphomicrobium*" can mean that the bacterium is classified into the genus *Hyphomicrobium* according to the classification known to a person skilled in the art of microbiology, although the bacterium is not particularly limited. Specifically, those classified into the group *Hyphomicrobium* according to the taxonomy used by the NCBI (National Center for Biotechnology Information) database (www.ncbi.nlm.nih.gov/Taxonomy/Browser/wwwtax.cgi) can be used. Examples of the bacterium belonging to the genus *Hyphomicrobium* include, but are not limited to, *Hyphomicrobium denitrificans* (*H. denitrificans*), *Hyphomicrobium aestuarii*, *Hyphomicrobium chloromethanicum*, *Hyphomicrobium denitrificans*, *Hyphomicrobium facile*, *Hyphomicrobium methylovorum*, *Hyphomicrobium vulgare*, *Hyphomicrobium* sp., etc.

Examples of PQQ-producing bacteria and parent strains which can be used to derive PQQ-producing bacteria include, but are not limited to, bacterial strains which inherently have the ability to produce PQQ. For example, parent strains which can be used to derive PQQ-producing bacteria can include, but are not limited to, strains belonging to the genus *Methylobacterium*, such as *M. mesophilicum* ATCC 29983, a pink-pigmented bacterium that utilizes L(−)-arabinose, D(−)-galalctose, D(−)-glucose, glycerol, sodium citrate, sodium glutamate, sodium malate, sodium malonate, sodium pyruvate, and sodium succinate as sole carbon sources for energy (Austin and Goodfellow. Int. J. Syst. Bacteriol. 29: 373-378, 1979), *M. extorquens* AM1 (ATCC 43645, DSM 1337, JCM 2802, ATCC 14718, DSM 1338, JCM 2805) (Urakami and Komagata. (1984) Int. J. Syst. Bacteriol. 34 (2): 188-201); *M. rhodesianum* JCM 2808 (ATCC 21612), and *M. rhodesianum* JCM 2809 (ATCC 21613) (Green, Bousfield, Hood. Int. J. Syst. Bacteriol 0.38, 124-127, 1988). Examples of parent strains belonging to the genus *Hyphomicrobium* can include the strains *H. variable* NCIB 10517 (US3989594 (A)); *H. vulgare* NCIB 9698 (Skerman et al. Int. J. Syst. Bacteriol. 30: 225-420, 1980), *H. methylovorum* IFO 14180 (ATCC 35216) (Izumi et al. J. Ferment. Technol. 60, 371-375, 1982); and *Hyphomicrobium* sp. DSM 1869 (ATCC 51888) that utilizes methanol, monomethylamine, dimethylamine, trimethylamine, pectin, acetate as sole carbon sources, and possess the possibility to utilize formate and ethanol (Urakami et al. Int. J. Syst. Bacteriol., 1995, 45, 528-532).

Above-mentioned strains are available from ATCC (American Type Culture Collection, 12301 Parklawn Drive, Rockville, Md. 20852, P.O. Box 1549, Manassas, Va. 20108, United States of America), DSMZ (German Collection of Microorganisms and Cell Cultures, Inhoffenstrase 7B, 38124, Braunschweig, Germany), JCM (Japan Collection of Microorganisms (RIKEN BioResource Center, 2-1 Hirosawa, Wako, Saitama 351-0198, Japan), or NCIMB (National Collections of Industrial and Marine Bacteria, Tony Research Station 135, Abbey Road, Aberdeen AB9 8DG, United Kingdom).

The phrase "enhancing the expression of the gene cluster and/or gene(s)" can mean that the expression of the gene cluster and/or gene(s) is higher than that of a non-modified strain, for example, a wild-type strain. Examples of such modifications can include increasing the copy number of the expressed gene cluster or gene per cell, increasing the expression level of the gene cluster or gene, and so forth. The copy number of an expressed gene cluster or gene is measured, for example, by restricting the chromosomal DNA followed by Southern blotting using a probe based on the gene sequence, fluorescence in situ hybridization (FISH), and the like. The level of gene cluster or gene expression can be measured by various known methods including Northern blotting, quantitative RT-PCR, and the like. Furthermore, wild-type non-modified strains can include, for example, *M. extorquens* AM1, or *H. denitrificans* ATCC51888.

Figure 1:
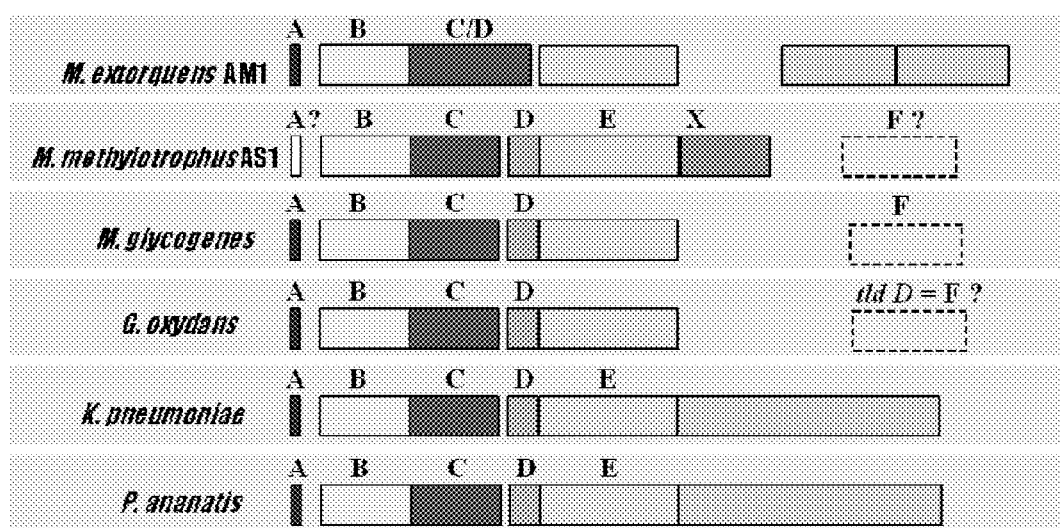
FIG. 1 shows PQQ biosynthesis gene clusters in various strains.

The term "pqq gene cluster" can mean a gene cluster or operon that encodes proteins involved in the PQQ biosynthesis. At present, for example, the sequences of the pqqADCDEF operon from *Klebsiella pneumoniae*, the pqqADCDE cluster from *Acinetobacter calcoaceticus*, the pqqADC/DE and pqqFG cluster from *Methylobacterium extorquens*, and the pqqADCDEF cluster from *Gluconobacter oxydans* have been disclosed. The schematic structures of pqq gene clusters from various microorganisms are shown in FIG. 1.

The genes encoding enzymes involving in PQQ biosynthesis in *M. extorquens* are known. *M. extorquens* contains a pqqABC/DE operon in which the pqqC and pqqD genes are fused, while the pqqFG genes form an operon with three other genes (Zhang et al. Microbiology 149:1033-1040 (2003)). The major pqqABC/DE operon is expressed under the control of one promoter located upstream of pqqA gene.

The term "pqqABC/DE operon from *Methylobacterium extorquens*" can mean a DNA that has a nucleotide sequence which includes the following structural genes: pqqA, pqqB, pqqCD, and pqqE genes, which encode a precursor and enzymes for PQQ biosynthesis.

The pqqA gene encodes a precursor for PQQ biosynthesis PqqA protein. The pqqA gene (nucleotides complementary to nucleotides in positions from 1825146 to 1825235; GenBank accession no. NC_012808.1; gi: 240136783) is located between the mxbM gene and the pqqB gene on the chromosome of *M. extorquens* strain AM1. The nucleotide sequence of the pqqA gene of the strain AM1 and the amino acid sequence of the PqqA protein encoded by the pqqA gene are shown in SEQ ID NO: 1 and SEQ ID NO: 2, respectively.

The pqqB gene encodes a PQQ synthesis protein PqqB with an unknown function. The pqqB gene (nucleotides complementary to nucleotides in positions from 1824199 to 1824891: GenBank accession no. NC_012808.1; gi: 240136783), is located between the pqqA gene and the pqqCD gene on the chromosome of *M. extorquens* strain AM1. The nucleotide sequence of the pqqB gene of the strain AM 1 and the amino acid sequence of the PqqB protein encoded by the pqqB gene are shown in SEQ ID NO: 3 and SEQ ID NO: 4, respectively.

The pqqCD gene encodes PQQ synthesis protein PqqCD. The pqqCD gene (nucleotides complementary to nucleotides in positions from 1822914 to 1824032: GenBank accession no. NC_012808.1; gi: 240136783) is located between the pqqB gene and the pqqE gene on the chromosome of *M. extorquens* strain AM1. The nucleotide sequence of the pqqCD gene of the strain AM1 and the amino acid sequence of the fused PqqCD protein encoded by the pqqCD gene are shown in SEQ ID NO: 5 and SEQ ID NO: 6, respectively.

The pqqE encodes PQQ synthesis protein PqqE with an unknown function. The pqqE gene (nucleotides complementary to nucleotides in positions from 1821763 to 1822887: GenBank accession no. NC_012808.1; gi: 240136783) is located between the pqqCD gene and the pqqE gene on the chromosome of the *M. extorquens* strain AM1. The nucleotide sequence of the pqqE gene of the strain AM1 and the amino acid sequence of the PqqE protein encoded by the pqqE gene are shown in SEQ ID NO: 7 and SEQ ID NO: 8, respectively.

The nucleotide sequence of the pqqABC/DE operon from *M. extorquens* AM1 is shown in SEQ ID NO: 9.

The complete genome sequences of several methylotrophic bacteria have been published recently. Analysis of the available genomes revealed the presence of additional copies of pqqA outside of the pqqABCDE cluster. In *M. extorquens* AM1, second and third copies located in tandem and presumably expressed under the control of one promoter, have been annotated. According to the present invention, one of the pqqA gene copies which is located between the serS gene, oriented in the opposite direction to the pqqA gene copies, and the other pqqA gene copy on the chromosome of *M. extorquens* AM1 (nucleotides in positions from 4753498 to 4753587: GenBank accession no. NC_012808.1; gi: 240136783), was given the name pqqA2 gene. The nucleotide sequence of the pqqA2 gene of the strain AM1 and the amino acid sequence of the PQQA2 protein encoded by the pqqA2 gene are shown in SEQ ID NO: 10 and SEQ ID NO: 11, respectively. Further according to the present invention, the other pqqA gene copy which is located between the pqqA2 gene and the MexAM1—META1p4630 gene, oriented in the opposite direction, on the chromosome of *M. extorquens* AM1 (nucleotides in positions from 4753650 to 4753739: GenBank accession no. NC_012808.1; gi: 240136783), was given the name pqqA3 gene. The nucleotide sequence of the pqqA3 gene of the strain AM1 and the amino acid sequence of the PQQA3 protein encoded by the pqqA3 gene are shown in SEQ ID NO: 12 and SEQ ID NO: 13, respectively.

The homology level between the PqqA, PqqA2 and PqqA3 proteins from *M. extorquens* AM1 is very high (see FIG. 2). Furthermore, inventors of the presently disclosed subject matter have examined available genome sequences of five strains of genera *Methylobacterium* and found that *M. chloromethanicum* CM4, *M. populi* BJ001, *M. radiotolerans* JCM2831 have the same organization of pqqA locus as *M. extorquens* AM1. *M. extorquens* DM4 has one additional copy of the pqqA gene located beyond the pqqABC/DE operon. *Methylobacterium* sp. 4-46 and *M. nodulans* ORS2060 have two copies of the pqqA gene located in the beginning of pqqABCDE cluster.

Computer analysis of the *Hyphomicrobium denitrificans* ATCC51888 genome revealed the presence of three gene copies of the pqqA gene which are located in different loci: the first pqqA gene copy (ORF Hden_1488), named according to the present invention the pqqA gene, is contained in a predicted pqqABCDE gene cluster, the second one (ORF Hden_0553), named according to the present invention the pqqA2 gene, is contained in a predicted pqqADE gene cluster, and the third one (ORF Hden_1488), named according to the present invention the pqqA3 gene, is located separately (see FIG. 7).

The term "pqqABCDE gene cluster from *Hyphomicrobium denitrificans*" can mean a nucleotide sequence which includes the following ORFs (ORF—open reading frame) encoding a precursor and putative PQQ biosynthesis enzymes: putative pqqA gene (Hden_1488), putative pqqB gene (Hden_1487), putative pqqC gene (Hden_1486), putative pqqD gene (Hden_1485), and putative pqqE gene (Hden_1484). The nucleotide sequence of the pqqA gene of *H. denitrificans* and the amino acid sequence of the putative PqqA protein encoded by the pqqA gene are shown in SEQ ID NO: 14 and SEQ ID NO: 15, respectively. The nucleotide sequence of the pqqB gene of *H. denitrificans* and the amino acid sequence of the putative PqqB protein encoded by the pqqB gene are shown in SEQ ID NO: 16 and SEQ ID NO: 17, respectively. The nucleotide sequence of the pqqC gene of *H. denitrificans* and the amino acid sequence of the putative PqqC protein encoded by the pqqC gene are shown in SEQ ID NO: 18 and SEQ ID NO: 19, respectively. The nucleotide sequence of the pqqD gene of *H. denitrificans* and the amino acid sequence of the putative PqqD protein encoded by the pqqD gene are shown in SEQ ID NO: 20 and SEQ ID NO: 21, respectively. The nucleotide sequence of the pqqE gene of *H. denitrificans* and the amino acid sequence of the putative PqqE protein encoded by the pqqE gene are shown in SEQ ID NO: 22 and SEQ ID NO: 23, respectively.

The nucleotide sequence of the pqqABCDE gene cluster from *H. denitrificans* ATCC51888 is shown in SEQ ID NO: 24.

The pqqA2 gene (synonym: Hden_0553) encodes a predicted PqqA protein. The pqqA2 gene (nucleotides complementary to nucleotides in positions from 585973 to 586080; GenBank accession no. NC_014313.1; gi: 300021538) is located between the Hden_0552 gene and the Hden_0554 gene on the chromosome of the *H. denitrificans* strain ATCC51888. The nucleotide sequence of the pqqA2 gene of the strain ATCC51888 and the amino acid sequence of the putative PqqA2 protein encoded by the pqqA2 gene are shown in SEQ ID NO: 25 and SEQ ID NO: 26, respectively.

The pqqA3 gene (synonym: Hden_2110) encodes a predicted PqqA protein. The pqqA3 gene (nucleotides complementary to nucleotides in positions from 2160533 to 2160432; GenBank accession no. NC_014313.1; gi: 300021538) is located between the Hden_2109 gene and the Hden_2111 gene, both oriented in opposite directions, on the chromosome of *H. denitrificans* strain ATCC51888. The nucleotide sequence of the pqqA3 gene of the strain ATCC51888 and the amino acid sequence of the putative PqqA3 protein encoded by the pqqA3 gene are shown in SEQ ID NO: 27 and SEQ ID NO: 28, respectively.

The term "pqqA-like gene" can mean a gene that is located in a bacterial genome and encodes a precursor for PQQ biosynthesis. According to the present invention, each of the above-described pqqA, pqqA2, and pqqA3 genes from *M. extorquens* AM1, also as pqqA, pqqA2, and pqqA3 genes from *H. denitrificans* ATCC51888, can be named "pqqA-like gene". The presence of a pqqA-like gene in a bacterial genome can be determined by analysis of the genome sequence, in addition to databases containing information about annotated pqqA genes from various microorganisms. pqqA-like genes from a wide range of microorganisms can be used. Examples of the bacterium containing in-genome pqqA-like gene are not limited to the above-mentioned methylotrophs. Examples of the bacterium containing in-genome pqqA-like genes can also include, *Methylococcus capsulatus* Bath, *Colwellia psychrerythraea* 34H, *Gluconobacter oxydans* 621H, *Methylobacillus flagellatus* KT, *Dinoroseobacter shibae* DFL 12, *Leptothrix cholodnii* SP-6, *Erwinia amylovora* ATCC 49946, *Acinetobacter* sp. RUH2624, *Saccharopolyspora erythraea* NRRL23338, *Bradyrhizobium* sp. ORS278, *Bradyrhizobium* sp. BTAi1/ATCC BAA-1182, *Ralstonia pickettii* 12J, *Pseudomonas fluorescensa*, etc. Some of the bacteria have multiple copies of pqqA-like gene in-genome, for instance, *Methylotenera mobilis* JLW8, *Methylovorus* sp. SIP3-4, *Methylobacterium extorquens* DM4, and *Methylobacterium* sp. 4-46.

Since there may be some differences in DNA sequences between the genera, species or strains, the gene cluster and the gene(s) which expression is/are enhanced are not limited to the genes shown in SEQ ID NO: 1, SEQ ID NO: 3, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 25, SEQ ID NO: 27, but can include genes homologous to SEQ ID NO: 1, SEQ ID NO: 3, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 25, SEQ ID NO: 27. Therefore, the protein variants encoded by the genes can have exemplary homology of not less than 80%, not less than 90%, or not less than 95%, with respect to the entire amino acid sequence shown in SEQ ID NO: 1, SEQ ID NO: 3, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 25, SEQ ID NO: 27, as long as the activity or function of the corresponding protein is maintained. The term "homology" may also be used to refer to "identity". The phrase "protein variant", as used in the presently disclosed subject matter, means proteins which have changes in the sequences, whether they are deletions, insertions, additions, or substitutions of amino acids. The number of changes in the variant proteins can depend on the position in the three dimensional structure of the proteins or the type of amino acid residues. Exemplary embodiments can be 1 to 30, 1 to 15, 1 to 5, or 1 to 3 in SEQ ID NO:2, SEQ ID NO:4, SEQ ID NO:6, SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:26, or SEQ ID NO:28. These changes in the variants can occur in regions of the protein which are not critical for the three dimensional structure of the protein. This is because some amino acids have high homology to one another so the three dimensional structure is not affected by such a change. An alignment of the PqqA homologues proteins from different microorganisms is shown on FIG. 2. It is known that PqqA peptides from various microorganisms include two conserved glutamate and tyrosine residues, which are separated by three amino acid residues (sequence motif -E-X-X-X-Y, SEQ ID NO: 52). Changes in the protein variants can occur in non-conservative regions.

The term "a protein having the function of PQQ precursor" can mean that the protein can be involved in PQQ biosynthesis as a precursor for PQQ, specifically, the protein can have a three dimensional structure which is sufficient to be recognized and used as a substrate by PQQ biosynthesis enzymes with subsequent conversion into PQQ.

Homology between two amino acid sequences can be determined using the well-known methods, for example, the computer program BLAST 2.0, which calculates three parameters: score, identity and similarity.

The substitution, deletion, insertion or addition of one or several amino acid residues should be conservative mutation(s) so that the activity or the function is maintained. The representative conservative mutation is a conservative substitution. Examples of conservative substitutions can include substitution of Ser or Thr for Ala, substitution of Gln, H is or Lys for Arg, substitution of Glu, Gln, Lys, H is or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Be, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Be or Leu for Val.

Therefore, the gene cluster and gene(s) can be a variant(s) which hybridizes under stringent conditions with the nucleotide sequence shown in SEQ ID NO: 1, SEQ ID NO: 3, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 25, SEQ ID NO: 27, or a probe which can be prepared from the nucleotide sequence, provided that it encodes a functional protein. "Stringent conditions" can include those under which a specific hybrid, for example, a hybrid having homology of not less than 60%, is formed and a non-specific hybrid, for example, a hybrid having homology lower than the above, is not formed. Other exemplary homologies can include not less than 70%, not less than 80%, not less than 90%, not less than 95%, and not less than 98%. For example, stringent conditions are exemplified by washing one time or more, such as two or three times, at a salt concentration of 1×SSC, 0.1% SDS. Another exemplary salt concentration can include 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. By way of example, washing can be performed 2 to 3 times. The length of the probe can be suitably selected depending on the hybridization conditions, and can be 100 by to 1 kbp, for example. Moreover, codons in the gene sequences may be replaced with other equivalent codons which are easily used in the host into which the genes are introduced.

Methods which can be used to enhance gene cluster and/or gene(s) expression include increasing the gene cluster and/or the gene(s) copy number, and introducing a gene cluster and/or a gene into a vector that is able to increase the copy number of the gene cluster and/or the gene in a bacterium of the *Methylobacterium* or *Hyphomicrobium* genera. Examples of vectors include but are not limited to broad-host-range vectors such as pCM110, pRK310, pVK101, pBBR122, pBHR1, and the like.

Enhancement of the gene cluster and/or gene expression can also be achieved by introducing multiple copies of the gene cluster and/or gene into a bacterial chromosome by, for example, homologous recombination, Mu integration, or the like. For example, one act of Mu integration allows for the introduction of up to 3 copies of the gene into a bacterial chromosome.

The copy number of gene cluster and/or gene can also be increased by introducing multiple copies of the gene into the chromosomal DNA of the bacterium. In order to introduce multiple copies of the gene cluster and/or the gene into the bacterial chromosome, homologous recombination can be carried out using a sequence with multiple copies of the sequence in the chromosomal DNA. Sequences with multiple copies in the chromosomal DNA include, but are not limited to, repetitive DNA, or inverted repeats present at the end of a transposable element. Also, it is possible to incorporate the gene cluster and/or the gene into a transposon, and allow it to be transferred to introduce multiple copies of the gene cluster and/or the gene into the chromosomal DNA.

Enhancing of the gene cluster and/or gene expression may also be achieved by placing the DNAs under the control of a potent promoter. For example, the lac promoter, the trp promoter, the trc promoter, the $P_R$, or the $P_L$ promoters of lambda phage are all known to be potent promoters. Potent promoters providing a high level of gene expression in a bacterium belonging to the genus *Hyphomicrobium* or *Methylobacterium* can be used. Especially, methanol dehydrogenase promoter $P_{mxaF}$ is known as a strong methanol-inducible promoter in *Methylobacterium*. The use of a potent promoter can be combined with multiplication of gene copies.

Alternatively, the effect of a promoter can be enhanced by, for example, introducing a mutation into the promoter to increase the transcription level of the gene cluster and/or the gene located downstream of the promoter. Furthermore, it is known that substitution of several nucleotides in the spacer between ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984).

Moreover, it is also possible to introduce a nucleotide substitution into the promoter region of the gene cluster and/or the gene on the bacterial chromosome, which results in a stronger promoter function.

Methods for preparation of plasmid DNA, digestion, and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

2. Method

The method for producing PQQ can be a method which includes the steps of cultivating the bacterium according to the presently disclosed subject matter in a culture medium to cause accumulation of PQQ in the medium, and collecting PQQ from the medium.

The cultivation, collection, and purification of the PQQ from the medium and the like may be performed in a manner similar to conventional fermentation methods wherein PQQ is produced using a bacterium.

The medium which can be used in the culture can be either a synthetic or natural medium, so long as the medium includes a carbon source, a nitrogen source, minerals and, if necessary, appropriate amounts of nutrients which the bacterium may require for growth. The carbon source can include various carbohydrates such as glucose and sucrose, various organic acids, alcohol including methanol, ethanol and glycerol. Methanol is the most preferable. The nitrogen source can include various ammonium salts such as ammonia and ammonium sulphate, other nitrogen compounds such as amines, a natural nitrogen source such as peptone, soybean-hydrolysate, and digested fermentative microorganism. The sulfur source can include ammonium sulphate, magnesium sulphate, ferrous sulphate, manganese sulphate, and the like. Minerals can include potassium monophosphate, sodium chloride, calcium chloride, and the like. Vitamins can include thiamine, yeast extract, and the like.

The cultivation can be performed under aerobic conditions such as a shaking culture or a stirring culture with aeration, at a temperature of 20 to 40° C., and in another example 25 to 37° C. The pH of the culture is usually between 5 and 9, and in another example between 6 and 8. The pH of the culture can be adjusted with ammonia, calcium carbonate, various acids, various bases, and buffers. Usually, a 1 to 5-day cultivation period leads to the accumulation of PQQ in the liquid medium.

After cultivation, solids such as cells can be removed from the liquid medium by centrifugation or membrane filtration, and the PQQ can be collected and purified by ion-exchange, concentration, and crystallization methods.

EXAMPLES

The present invention will be more concretely explained below with reference to the following non-limiting examples.

Example 1

Construction of Plasmids Containing PQQ Biosynthesis Genes from M. extorquens

Construction of the Plasmid pPQQ1

The plasmid pPQQ1 was constructed for overexpression of pqqABC/DE operon from M. extorquens AM1 (FIG. 5). For this purpose, plasmid pHT1 (FIG. 3; Toyama H, Lidstrom M E. Microbiology. 1998 January; 144 (Pt 1):183-91)) was treated with restrictases BamHI and XhoI followed by treatment with a Klenow fragment of DNA-polymerase I. After that, the 6.2 kb blunted BamHI-XhoI fragment containing pqqABC/DE operon and gene mxbM encoding the positive regulator of the pqq genes from M. extorquens was cloned into the region between BamHI-Ec1136II sites of vector pCM110 (FIG. 4, the GenBank accession number for this cloning vector is AF327718) to produce plasmid pQQ1 (FIG. 5). The ligated mixture was transformed to E. coli TG1 strain (DSM 6056) and plasmid DNA was isolated from the clones grown on LB plates with tetracyclin (10 μg/ml). The plasmids of the expected structure were selected using restriction analysis. The resulting plasmid was given the name pQQ1. E. coli TG1 strain is available from DSMZ (German Collection of Microorganisms and Cell Cultures, Inhoffenstrase 7B, 38124, Braunschweig, Germany).

To check whether the mxbM gene overexpression had an affect on PQQ production, the second plasmid pPQQ2 without promoter $P_{mxaF}$ was constructed. Deletion of $P_{mxaF}$ was obtained as following: the plasmid pPQQ1 was digested with restrictases BamHI and PstI, blunt-ended, and then self-ligated. The resulting plasmid contained pqqABC/DE operon expressing under the control of the native promoter which is located on the plasmid downstream of the gene mxbM. The construction of strains M. extorquens/pPQQ1 and M. extorquens/pPQQ2, and assay of the amount of produced PQQ, were conducted as described in Example 3. The strains M. extorquens AM1/pPQQ1 and M. extorquens AM1/pPQQ2 showed a nearly identical amount of accumulated PQQ (see Table1). Thus, according to the obtained data, enhancing the mxbM gene expression does not significantly contribute to increasing PQQ production by the strain with enhanced expression of the pqq genes. Plasmid pPQQ1 was used for the further experiments.

TABLE 1

| Strain | PQQ, mg/l (HPLC) |
|---|---|
| M. extorquens AM1/pPQQ1 | 52.5 ± 0.7 |
| M. extorquens AM1/pPQQ2 | 53.5 ± 0.7 |

2. Construction of the Plasmid pPQQ1pqqA2A3

The plasmid pPQQ1pqqA2A3 was constructed for overexpression of pqqABC/DE operon and two pqqA gene copies—the pqqA2 gene and the pqqA3 gene, from M. extorquens AM1. For this purpose, DNA fragment containing the pqqA2 and pqqA3 genes under transcriptional control of its own promoter was generated by PCR using primers EG539 (SEQ ID NO: 29) and EG540 (SEQ ID NO: 30). Chromosome DNA isolated from the M. extorquens AM1 was used as the template in the reaction. The temperature profile was the following: initial DNA denaturation for 5 min at 95° C., followed by 30 cycles of denaturation at 95° C. for 30 sec, annealing at 57° C. for 30 sec, elongation at 72° C. for 2 min, and the final elongation for 5 min at 72° C.

The obtained 1.1 kb fragment was purified followed by treatment with PstI restrictase, and cloned into SwaI-PstI sites of the pPQQ1 plasmid to produce pPQQ1pqqA2A3 (FIG. 6). The ligated mixture was transformed to E. coli TG1 strain and plasmid DNA was isolated from the clones grown on LB plates with tetracyclin (10 μg/ml). The plasmids of the expected structure have been selected using restriction analysis. The resulting plasmid was given the name pQQ1pqqA2A3.

Example 2

Construction of Plasmids Containing PQQ Biosynthesis Genes from Hyphomicrobium denitrificans Construction of the plasmid pHABCDE.

The plasmid pHABCDE was constructed for overexpression of pqqABCDE gene cluster from H. denitrificans ATCC51888 (DSM1869) (the strain was obtained from German Collection of Microorganisms and Cell Cultures (DSMZ)). For this purpose, DNA fragment containing pqqABCDE gene cluster was generated by PCR using primers EG572 (SEQ ID NO: 35) and EG573 (SEQ ID NO: 36). Chromosome DNA isolated from the H. denitrificans ATCC51888 was used as the template in the reaction. The temperature profile was the following: initial DNA denaturation for 5 min at 95° C., followed by 30 cycles of denaturation at 95° C. for 30 sec, annealing at 57° C. for 30 sec, elongation at 72° C. for 2 min and the final elongation for 5 min at 72° C.

The obtained 3.7 kb fragment was purified followed by treatment with BamHI and SacI restrictases, and ligated into the pCM110 plasmid which had been previously treated with the same endonucleases, to produce pHABCDE (FIG. 8). The ligated mixture was transformed to E. coli TG1 strain and plasmid DNA was isolated from the clones grown on LB plates with tetracyclin (10 μg/ml). The plasmids of the expected structure have been selected using restriction analysis. The resulting plasmid was given the name pHABCDE.

2. Construction of Plasmid pHABCDEA3.

The plasmid pHABCDEA3 was constructed for overexpression of pqqABCDE gene cluster and pqqA3 gene from *H. denitrificans* ATCC51888. For this purpose, DNA fragment containing pqqA3 gene was generated by PCR using primers EG568 (SEQ ID NO: 31) and EG569 (SEQ ID NO: 32). Chromosome DNA isolated from the *H. denitrificans* ATCC51888 was used as the template in the reaction. The temperature profile was the following: initial DNA denaturation for 5 min at 95° C., followed by 30 cycles of denaturation at 95° C. for 30 sec, annealing at 57° C. for 30 sec, elongation at 72° C. for 2 min and the final elongation for 5 min at 72° C.

The obtained 0.27 kb fragment was purified followed by treatment with XbaI restrictase, and cloned between the XbaI and SwaI sites of the plasmid pHABCDE to produce pHABCDEA3 (FIG. 9). The ligated mixture was transformed to *E. coli* TG1 strain and plasmid DNA was isolated from the clones grown on LB plates with tetracyclin (10 μg/ml). The plasmids of the expected structure have been selected using restriction analysis. The resulting plasmid was given the name pHABCDEA3.

3. Construction of the Plasmid pHABCDEA2A3.

The plasmid pHABCDEA2A3 was constructed for overexpression of the pqqA3 and pqqA2 genes from *H. denitrificans* in addition to pqqABCDE gene cluster. For this purpose, a DNA fragment containing pqqA2 gene was generated by PCR using primers EG570 (SEQ ID NO: 33) and EG571 (SEQ ID NO: 34). Chromosome DNA isolated from the *H. denitrificans* ATCC51888 was used as the template in the reaction. The temperature profile was the following: initial DNA denaturation for 5 min at 95° C., followed by 30 cycles of denaturation at 95° C. for 30 sec, annealing at 57° C. for 30 sec, elongation at 72° C. for 2 min and the final elongation for 5 min at 72° C.

The obtained 0.36 kb fragment was purified followed by treatment with XbaI and BamHI restrictases, and cloned between the BamHI and XbaI sites of the plasmid pHABCDEA3 to produce pHABCDEA2A3 (FIG. 10). The ligated mixture was transformed to *E. coli* TG1 strain and plasmid DNA was isolated from the clones grown on LB plates with tetracyclin (10 μg/ml). The plasmids of the expected structure have been selected using restriction analysis. The resulting plasmid was given the name pHABCDEA2A3.

Example 3

Production of PQQ by *M. extorquens* Strains AM1/pPQQ1 and AM1/pPQQ1pqqA2A3

To test the effect of the enhanced expression of the pqqA2 and pqqA3 genes and pqqABC/DE operon from *M. extorquens* AM1 on PQQ production, plasmids pPQQ1 and pPQQ1pqqA2A3 were transferred in PQQ-producing strain *M. extorquens* AM1 by biparental mating using *E. coli* strain S17-1 (ATCC 47055), bearing the respective plasmids, as described by Abalakina et al. (Abalakina et al. Appl Microbiol Biotechnol.; 81(1):191-200 (2008)), with some modifications: Hypho medium (Harder, Attwood, and Quayle. J. Gen. Microbiol. 78 155-163 (1973)) with 1% of methanol and supplemented with 10 ml/l of vitamin stock solution of following composition: biotin 2.0 mg/l, folic acid 2.0 mg/l, thiamine-HCl 5.0 mg/l, Ca pantothenate 5.0 mg/l, B 12 0.1 mg/l, riboflavin 5.0 mg/l, nicotinamide 5.0 mg/l; was used for *M. extorquens* strains cultivation.

The obtained *M. extorquens* strains, AM1/PQQ1 and AM1/pPQQ1pqqA2A3, and control strain AM1, were separately cultivated for 60 hours on the plate of supplemented Hypho medium (as described above), one loop (from ⅛ plate) of the grown biomass were used as seed cultures, each of the cultures were inoculated into 5 ml of the supplemented Hypho medium, and were each cultivated at 30° C. for 72 hours with a rotary shaker at 240 rpm. For maintenance of the plasmid, 10 μg/ml of tetracycline was supplemented during the course of cultivation.

After the cultivation, the amount of PQQ which had accumulated in the medium was determined by HPLC analysis. The analytic conditions for HPLC were the following: column: Inertsil ODS-3(4 μm, 150 mm×4.6 mm I.D); eluents: (A) $CH_3OH$, (B) 15 mM TBA solution, A/B=50/50 (V/V) gradient mixer; flow rate: 1.0 ml/min; column temperature: 40° C.; detection UV250 nm or FL Ex 360 nm Em 455 nm; injection vol.: 5 μl. TBA solution: Tetra-butylammonium (4.8 g) is solved in water (1 L) and pH is adjusted to 3.5 by phosphate. Additionally, an optical density of each culture at 600 nm (OD 600) was measured.

The results of the test tube fermentations are shown in Table 2 and in Table 3. As it can be seen from Table 2, *M. extorquens* strain AM1/pPQQ1 with enhanced expression of the pqqABC/DE operon from *M. extorquens* AM1 demonstrated an 8-fold higher amount of accumulation of PQQ as compared with the parent strain. As it can be seen from Table 3, strain AM1/pPQQ1pqqA2A3 with enhanced expression of the pqqA2 and pqqA3 genes in addition to the pqqABC/DE operon, demonstrated a doubled amount of accumulation of PQQ as compared with the strain *M. extorquens* AM1/pPQQ1.

TABLE 2

| Strain | $OD_{600\,nm}$ | PQQ, mg/l (HPLC) |
|---|---|---|
| *M. extorquens* AM1 | 7.9 | 3.9 |
| *M. extorquens* AM1/pPQQ1 | 8.6 ± 0.9 | 31.4 ± 1 |

TABLE 3

| Strain | $OD_{600\,nm}$ | PQQ, mg/l (HPLC) |
|---|---|---|
| *M. extorquens* AM1/pPQQ1 | 10.7 | 50.0 |
| *M. extorquens* AM1/pPQQ1pqqA2A3 | 11.5 ± 0.1 | 114.0 ± 2.8 |

Example 4

Production of PQQ by *H. denitrificans* Strains ATCC51888/pHABCDE, ATCC51888/pHABCDEA3, and ATCC51888/pHABCDEA2A3

To test the effect of the enhanced expression of the pqqA2 and pqqA3 genes and pqqABCDE gene cluster from *H. denitrificans* on PQQ production, plasmids pHABCDE, pHABCDEA3, and pHABCDEA2A3 were transferred into *H. denitrificans* strain ATCC51888 by biparental mating using *E. coli* strain S 17-1 bearing the respective plasmids as described by Abalakina et al. (Abalakina et al. Appl Microbiol Biotechnol.; 81(1):191-200 (2008)), with some modifications: B medium (Urakami et al. Applied And Environmental Microbiology, Vol. 58, No12, p. 3970-3976, 1992) with 1% of methanol was used for *H. denitrificans* strains cultivation.

The obtained *H. denitrificans* strains, ATCC51888/pHABCDE, ATCC51888/pHABCDEA3, ATCC51888/pHABCDEA2A3, and the control strain ATCC51888, were separately cultivated for 60 hours on the plate of B medium and one loop (from ⅛ plate) of biomass grown were used as seed cultures, each of the cultures were inoculated into 5 ml of the B medium, and were each cultivated at 30° C. for 72 hours with a rotary shaker at 240 rpm. For maintenance of the plasmid, 10 μg/ml of tetracycline was supplemented during the course of cultivation.

After the cultivation, the amount of PQQ which had accumulated in the medium was determined by HPLC analysis, as described above.

The results of the test tube fermentations are shown in Table 4. As it can be seen from Table 4, *H. denitrificans* strain ATCC51888/pHABCDE with enhanced expression of the pqqABCDE gene cluster from *H. denitrificans* demonstrated a higher amount of accumulation of PQQ as compared with the parent strain ATCC51888. The strain *H. denitrificans* ATCC51888/pHABCDEA3 with enhanced expression of the pqqA3 gene from *H. denitrificans* also demonstrated a higher amount of accumulation of PQQ as compared with the parent strain and the strain ATCC51888/pHABCDE. The strain ATCC51888/pHABCDEA2A3 with enhanced expression of the pqqA2 and pqqA3 genes in addition to pqqABCDE gene cluster demonstrated the highest amount of accumulation of PQQ.

TABLE 4

| Strain | PQQ, mg/l (HPLC) |
|---|---|
| *H. denitrificans* ATCC51888 | 7.5 ± 0.1 |
| *H. denitrificans* ATCC51888/pHABCDE | 9.6 ± 0.1 |
| *H. denitrificans* ATCC51888/pHABCDEA3 | 10.2 ± 0.1 |
| *H. denitrificans* ATCC51888/pHABCDEA2A3 | 10.9 ± 0.1 |

Example 5

Production of PQQ by *H. denitrificans* Strains ATCC51888/pQQ1 and ATCC51888/PQQ1A2A3

To test the effect of the enhanced expression of the pqqA2 and pqqA3 genes, and pqqABC/DE operon from *M. extorquens* AM1, on PQQ production by *H. denitrificans*, plasmids pPQQ1 and pPQQ1pqqA2A3 were transferred into *H. denitrificans* strain ATCC51888 by biparental mating using *E. coli* strain S 17-1 bearing the respective plasmids as described by Abalakina et al. (Abalakina et al. Appl Microbiol Biotechnol.; 81(1):191-200 (2008)), with some modifications: B medium (Urakami et al. Applied And Environmental Microbiology, Vol. 58, No12, p. 3970-3976, 1992) with 1% of methanol was used for *H. denitrificans* strains cultivation.

Both *H. denitrificans* strains, ATCC51888/pQQ1 and ATCC51888/pQQ1A2A3, were separately cultivated for 60 hours on a plate of B medium, and one loop (from ⅛ plate) of biomass grown on each plate was used as a seed culture. Each of the cultures were inoculated into 5 ml of the B medium, and cultivated at 30° C. for 72 hours with a rotary shaker at 240 rpm. For maintenance of the plasmid, 10 μg/ml of tetracycline was supplemented during the course of cultivation.

After the cultivation, the amount of PQQ which had accumulated in the medium was determined by HPLC analysis, as described above.

The results of the test tube fermentations are shown in Table 5. As it can be seen from Table 5, *H. denitrificans* strain ATCC51888/pQQ1 with enhanced expression of the pqqABC/DE operon from *M. extorquens* AM1 demonstrated a higher amount of accumulation of PQQ as compared with the parent strain *H. denitrificans* ATCC51888. The strain *H. denitrificans* ATCC51888/pQQ1pqqA2pqqA3 with enhanced expression of the pqqA2 and pqqA3 genes from *M. extorquens* AM1 in addition to the pqqABC/DE operon demonstrated a higher amount of accumulation of PQQ as compared with the parent strain and the strain ATCC51888/pQQ1.

TABLE 5

| Strain | PQQ, mg/l (HPLC) |
|---|---|
| *H. denitrificans* ATCC51888 | 7.5 ± 0.1 |
| *H. denitrificans* ATCC51888/pPQQ1 | 8.3 ± 0.1 |
| *H. denitrificans* ATCC51888/pPQQ1pqqA2A3 | 10.6 ± 0.1 |

While the invention has been described in detail with reference to preferred embodiments thereof, it will be apparent to one skilled in the art that various changes can be made, and equivalents employed, without departing from the scope of the invention. All documents cited herein are hereby incorporated by reference.

Industrial Applicability

According to the present invention, pyrroloquinoline quinine is produced by a bacterium belonging to the genus *Methylobacterium* or *Hyphomicrobium*.

Explanation of Sequence Listing

SEQ ID NO: 1: nucleotide sequence of pqqA of *M. extorquens* AM1

SEQ ID NO: 2: amino acid sequence of PqqA of *M. extorquens* AM1, C7C9M1, B1LV85

SEQ ID NO: 3: nucleotide sequence of pqqB of *M. extorquens* AM1

SEQ ID NO: 4: amino acid sequence of PqqB of *M. extorquens* AM1

SEQ ID NO: 5: nucleotide sequence of pqqCD of *M. extorquens* AM1

SEQ ID NO: 6: amino acid sequence of PqqCD of *M. extorquens* AM1

SEQ ID NO: 7: nucleotide sequence of pqqE of *M. extorquens* AM1

SEQ ID NO: 8: amino acid sequence of PqqE of *M. extorquens* AM1

SEQ ID NO: 9: nucleotide sequence of pqqABC/DE operon of *M. extorquens* AM1

SEQ ID NO: 10: nucleotide sequence of pqqA2 of *M. extorquens* AM1

SEQ ID NO: 11: amino acid sequence of PQQA2 of *M. extorquens* AM1, C7CLK2

SEQ ID NO: 12: nucleotide sequence of pqqA3 of *M. extorquens* AM1

SEQ ID NO: 13: amino acid sequence of PQQA3 of *M. extorquens* AM1

SEQ ID NO: 14: nucleotide sequence of putative pqqA of *H. denitrificans*

SEQ ID NO: 15: amino acid sequence of putative PqqA of *H. denitrificans*

SEQ ID NO: 16: nucleotide sequence of putative pqqB of *H. denitrificans*

SEQ ID NO: 17: amino acid sequence of putative PqqB of *H. denitrificans*

SEQ ID NO: 18: nucleotide sequence of putative pqqC of *H. denitrificans*

SEQ ID NO: 19: amino acid sequence of putative PqqC of *H. denitrificans*

SEQ ID NO: 20: nucleotide sequence of putative pqqD of *H. denitrificans*

SEQ ID NO: 21: amino acid sequence of putative PqqD of *H. denitrificans*
SEQ ID NO: 22: nucleotide sequence of putative pqqE of *H. denitrificans*
SEQ ID NO: 23: amino acid sequence of putative PqqE of *H. denitrificans*
SEQ ID NO: 24: nucleotide sequence of pqqABCDE gene cluster of *H. denitrificans* ATCC51888
SEQ ID NO: 25: nucleotide sequence of putptive pqqA2 of *H. denitrificans* strain ATCC51888
SEQ ID NO: 26: amino acid sequence of putative PqqA2 of *H. denitrificans* strain ATCC51888
SEQ ID NO: 27: nucleotide sequence of putptive pqqA3 of *H. denitrificans* strain ATCC51888
SEQ ID NO: 28: amino acid sequence of putative PqqA3 of *H. denitrificans* strain ATCC51888
SEQ ID NO: 29: primer EG539
SEQ ID NO: 30: primer EG540
SEQ ID NO: 31: primer EG568
SEQ ID NO: 32: primer EG569
SEQ ID NO: 33: primer EG570
SEQ ID NO: 34: primer EG571
SEQ ID NO: 35: primer EG572
SEQ ID NO: 36: primer EG573
SEQ ID NO: 37: Q4KEK3
SEQ ID NO: 38: Q4K4V2
SEQ ID NO: 39: B2UEV0
SEQ ID NO: 40: B2U9I4
SEQ ID NO: 41: C6WTX0, D7DHP0
SEQ ID NO: 42: A4YZY3
SEQ ID NO: 43: A4YZ28
SEQ ID NO: 44: A4YNW1
SEQ ID NO: 45: Q608P4
SEQ ID NO: 46: Q488A4
SEQ ID NO: 47: Q9L3B4
SEQ ID NO: 48: Q1GX88
SEQ ID NO: 49: A8LN54
SEQ ID NO: 50: D41FL0
SEQ ID NO: 51: B1Y7S1
SEQ ID NO: 52: sequence motif -E-X-X-X-Y

The invention claimed is:

1. A method for producing pyrroloquinoline quinone (PQQ) comprising:
   A) cultivating in a culture medium a bacterium belonging to the genus *Hyphomicrobium*, and
   B) collecting PQQ from the culture medium,
   wherein the bacterium has been modified to enhance expression of a pqqABCDE gene cluster from *Hyphomicrobium dentirificans* by a method selected from the group consisting of:
      (i) increasing the copy number of the gene cluster,
      (ii) introducing multiple copies of the gene cluster into the chromosome of said bacterium,
      (iii) placing the gene cluster under the control of a potent promoter, and
      (iv) combinations thereof.

2. The method according to claim 1, wherein said pqqABCDE gene cluster comprises DNA comprising the nucleotide sequences of SEQ ID NO: 14, SEQ ID NO: 16, SEQ ID NO: 18, SEQ ID NO: 20, and SEQ ID NO: 22, or variants thereof.

3. The method according to claim 1, wherein said bacterium is *Hyphomicrobium denitrificans*.

4. The method according to claim 1, wherein said culture medium comprises methanol as a carbon source.

5. A method for producing pyrroloquinoline quinone (PQQ) comprising:
   A) cultivating in a culture medium a bacterium belonging to the genus *Methylobacterium* or *Hyphomicrobium*, and
   B) collecting PQQ from the culture medium,
   wherein said bacterium has been modified to have enhanced expression of a pqq gene cluster by a method selected from the group consisting of:
      (i) increasing the copy number of the gene cluster,
      (ii) introducing multiple copies of the gene cluster into the chromosome of said bacterium,
      (iii) placing the gene cluster under the control of a potent promoter, and
      (iv) combinations thereof,
   and has been further modified to enhance expression of a pqqA-like gene selected from the group consisting of:
      a DNA that encodes a protein comprising the amino acid sequence of SEQ ID NO: 11;
      a DNA that encodes a protein comprising the amino acid sequence of SEQ ID NO: 11, but that contains substitutions, deletions, insertions, additions or inversions of one or two amino acid residues and comprises a sequence motif -E-X-X-X-Y (SEQ ID NO: 52), and said protein has the function of PQQ precursor;
      a DNA that encodes a protein comprising the amino acid sequence of SEQ ID NO: 13;
      a DNA that encodes a protein comprising the amino acid sequence of SEQ ID NO: 13, but that contains substitutions, deletions, insertions, additions or inversions of one or two amino acid residues and comprises a sequence motif -E-X-X-X-Y (SEQ ID NO: 52), and said protein has the function of PQQ precursor;
      a DNA that encodes a protein comprising the amino acid sequence of SEQ ID NO: 26;
      a DNA that encodes a protein comprising the amino acid sequence SEQ ID NO: 26, but that contains substitutions, deletions, insertions, additions or inversions of one or two amino acid residues and comprises a sequence motif -E-X-X-X-Y (SEQ ID NO: 52), and said protein has the function of PQQ precursor;
      a DNA that encodes a protein comprising the amino acid sequence of SEQ ID NO: 28;
      a DNA that encodes a protein comprising the amino acid sequence of SEQ ID NO: 28, but that contains substitutions, deletions, insertions, additions or inversions of one or two amino acid residues and comprises a sequence motif -E-X-X-X-Y (SEQ ID NO: 52), and said protein has the function of PQQ precursor, and combinations thereof;
   wherein said expression is enhanced by a method selected from the group consisting of:
      (i) increasing the copy number of said pqqA-like gene,
      (ii) introducing multiple copies of said pqqA-like gene into the chromosome of said bacterium,
      (iii) placing said pqqA-like gene under the control of a potent promoter, and
      (iv) combinations thereof.

6. The method according to claim 5, wherein said pqq gene cluster is the pqqABC/DE operon from *Methylobacterium extorquens*.

7. The method according to claim 6, wherein said pqqABC/DE operon comprises DNA comprising the nucleotide sequences of SEQ ID NO: 1, SEQ ID NO: 3, SEQ ID NO: 5, and SEQ ID NO: 7, or variants thereof.

8. The method according to claim 5, wherein said pqq gene cluster is the pqqABCDE cluster from *Hyphomicrobium denitrificans*.

9. The method according to claim 8, wherein said pqqABCDE cluster comprises DNA comprising nucleotide sequences of SEQ ID NO: 14, SEQ ID NO: 16, SEQ ID NO: 18, SEQ ID NO: 20, and SEQ ID NO: 22, or variants thereof.

10. The method according to claim 5, wherein said bacterium is *Hyphomicrobium denitrificans*.

11. The method according to claim 5, wherein said bacterium is *Methylobacterium extorquens*.

12. The method according to claim 5, wherein said culture medium comprises methanol as a carbon source.

* * * * *

```
                        SEQUENCE LISTING

<160> NUMBER OF SEQ ID NOS: 52

<210> SEQ ID NO 1
<211> LENGTH: 90
<212> TYPE: DNA
<213> ORGANISM: Methylobacterium extorquens
<220> FEATURE:
<221> NAME/KEY: CDS
<222> LOCATION: (1)..(90)

<400> SEQUENCE: 1 atg aag tgg gct gcc ccc atc gtt tcc gag atc tgc gtc ggc atg gaa    48
Met Lys Trp Ala Ala Pro Ile Val Ser Glu Ile Cys Val Gly Met Glu
1               5                   10                  15 gtc acg agc tac gag tcg gcc gag atc gac acc ttc aac taa            90
Val Thr Ser Tyr Glu Ser Ala Glu Ile Asp Thr Phe Asn
                20                  25

<210> SEQ ID NO 2
<211> LENGTH: 29
<212> TYPE: PRT
<213> ORGANISM: Methylobacterium extorquens

<400> SEQUENCE: 2

Met Lys Trp Ala Ala Pro Ile Val Ser Glu Ile Cys Val Gly Met Glu
1               5                   10                  15

Val Thr Ser Tyr Glu Ser Ala Glu Ile Asp Thr Phe Asn
                20                  25

<210> SEQ ID NO 3
<211> LENGTH: 693
<212> TYPE: DNA
<213> ORGANISM: Methylobacterium extorquens
<220> FEATURE:
<221> NAME/KEY: CDS
<222> LOCATION: (1)..(693)

<400> SEQUENCE: 3 atg cat ccg cgc gag ggc ctg cgc cac tcg ccg atc cac gcg gtg ctg    48
Met His Pro Arg Glu Gly Leu Arg His Ser Pro Ile His Ala Val Leu
1               5                   10                  15 ctg acg aac ggc gac gtc gat cac gtt gcg ggc ctg ctg acc ctg cgc    96
Leu Thr Asn Gly Asp Val Asp His Val Ala Gly Leu Leu Thr Leu Arg
                20                  25                  30
```

```
gag ggc cag ccc ttc acg ctc tac gcg aca ccc ggc atc ctg gcc tcc      144
Glu Gly Gln Pro Phe Thr Leu Tyr Ala Thr Pro Gly Ile Leu Ala Ser
             35                  40                  45 gtc tcc gac aac cgc gtc ttc gac gtg atg gcc gcc gac gtg gtg aag      192
Val Ser Asp Asn Arg Val Phe Asp Val Met Ala Ala Asp Val Val Lys
 50                  55                  60 cgg cag acg atc gcc ctc aac gag acc ttc gag ccg gtc ccc ggc ctc      240
Arg Gln Thr Ile Ala Leu Asn Glu Thr Phe Glu Pro Val Pro Gly Leu
 65                  70                  75                  80 tcg gtg acg ctg ttc tcc gtc ccc ggc aag gtg ccg ctc tgg ctg gaa      288
Ser Val Thr Leu Phe Ser Val Pro Gly Lys Val Pro Leu Trp Leu Glu
                 85                  90                  95 gac gcc tcg atg gag atc ggg gcg gag acc gaa acc acg gtc ggc acg      336
Asp Ala Ser Met Glu Ile Gly Ala Glu Thr Glu Thr Thr Val Gly Thr
                100                 105                 110 atg atc gag gcc ggg ggc aag cgc ctc gcc tac atc ccc ggc tgc gcc      384
Met Ile Glu Ala Gly Gly Lys Arg Leu Ala Tyr Ile Pro Gly Cys Ala
            115                 120                 125 cgg gtg acg gag gat ctc aaa gcc cgc atc gcc ggc gca gac gcg ctc      432
Arg Val Thr Glu Asp Leu Lys Ala Arg Ile Ala Gly Ala Asp Ala Leu
130                 135                 140 ctg ttc gac ggc acg gtg ctg gag gac gac gac atg atc cgc gcc ggt      480
Leu Phe Asp Gly Thr Val Leu Glu Asp Asp Asp Met Ile Arg Ala Gly
145                 150                 155                 160 gtc ggc acc aag acc ggc tgg cgc atg ggc cat atc cag atg aac ggc      528
Val Gly Thr Lys Thr Gly Trp Arg Met Gly His Ile Gln Met Asn Gly
                165                 170                 175 gag acc ggc tcg atc gcg tct ctc gcc gat atc gag atc ggc cga cgg      576
Glu Thr Gly Ser Ile Ala Ser Leu Ala Asp Ile Glu Ile Gly Arg Arg
            180                 185                 190 gtc ttc gtt cac atc aac aac acc aat ccg gtc ctg atc gag gat tcg      624
Val Phe Val His Ile Asn Asn Thr Asn Pro Val Leu Ile Glu Asp Ser
        195                 200                 205 tac gag cgc gcg agc gtc gag gcg cgc ggc tgg acc gtc gcc cat gac      672
Tyr Glu Arg Ala Ser Val Glu Ala Arg Gly Trp Thr Val Ala His Asp
210                 215                 220 ggc ctg acc ctc gat ctc tga                                           693
Gly Leu Thr Leu Asp Leu
225                 230

<210> SEQ ID NO 4
<211> LENGTH: 230
<212> TYPE: PRT
<213> ORGANISM: Methylobacterium extorquens

<400> SEQUENCE: 4

Met His Pro Arg Glu Gly Leu Arg His Ser Pro Ile His Ala Val Leu
 1               5                  10                  15

Leu Thr Asn Gly Asp Val Asp His Val Ala Gly Leu Leu Thr Leu Arg
            20                  25                  30

Glu Gly Gln Pro Phe Thr Leu Tyr Ala Thr Pro Gly Ile Leu Ala Ser
        35                  40                  45

Val Ser Asp Asn Arg Val Phe Asp Val Met Ala Ala Asp Val Val Lys
 50                  55                  60

Arg Gln Thr Ile Ala Leu Asn Glu Thr Phe Glu Pro Val Pro Gly Leu
 65                  70                  75                  80

Ser Val Thr Leu Phe Ser Val Pro Gly Lys Val Pro Leu Trp Leu Glu
                85                  90                  95
```

```
Asp Ala Ser Met Glu Ile Gly Ala Glu Thr Glu Thr Val Gly Thr
            100                 105                 110

Met Ile Glu Ala Gly Gly Lys Arg Leu Ala Tyr Ile Pro Gly Cys Ala
        115                 120                 125

Arg Val Thr Glu Asp Leu Lys Ala Arg Ile Ala Gly Ala Asp Ala Leu
    130                 135                 140

Leu Phe Asp Gly Thr Val Leu Glu Asp Asp Met Ile Arg Ala Gly
145                 150                 155                 160

Val Gly Thr Lys Thr Gly Trp Arg Met Gly His Ile Gln Met Asn Gly
                165                 170                 175

Glu Thr Gly Ser Ile Ala Ser Leu Ala Asp Ile Glu Ile Gly Arg Arg
            180                 185                 190

Val Phe Val His Ile Asn Asn Thr Asn Pro Val Leu Ile Glu Asp Ser
        195                 200                 205

Tyr Glu Arg Ala Ser Val Glu Ala Arg Gly Trp Thr Val Ala His Asp
    210                 215                 220

Gly Leu Thr Leu Asp Leu
225                 230

<210> SEQ ID NO 5
<211> LENGTH: 1119
<212> TYPE: DNA
<213> ORGANISM: Methylobacterium extorquens
<220> FEATURE:
<221> NAME/KEY: CDS
<222> LOCATION: (1)..(1119)

<400> SEQUENCE: 5 atg acc gcc caa ttc ccg ccg ccc gtc ccg gac acc gag caa cgc ctg    48
Met Thr Ala Gln Phe Pro Pro Pro Val Pro Asp Thr Glu Gln Arg Leu
1               5                   10                  15 ctg agc cac gag gag ctt gag gcg gcg ctc cgc gat atc ggt gca cgg    96
Leu Ser His Glu Glu Leu Glu Ala Ala Leu Arg Asp Ile Gly Ala Arg
            20                  25                  30 cgc tac cac aac ctc cac ccg ttc cac cgg ctg ctg cac gac ggc aag   144
Arg Tyr His Asn Leu His Pro Phe His Arg Leu Leu His Asp Gly Lys
        35                  40                  45 ctg tcg aag gat cag gtc cgg gcc tgg gcg ctc aac cgc tac tat tat   192
Leu Ser Lys Asp Gln Val Arg Ala Trp Ala Leu Asn Arg Tyr Tyr Tyr
    50                  55                  60 cag gcg atg att ccg gtg aag gat gca gcg ctg ctg gct cgc ctg ccg   240
Gln Ala Met Ile Pro Val Lys Asp Ala Ala Leu Leu Ala Arg Leu Pro
65                  70                  75                  80 gat gcg cag ctt cgc cga atc tgg cgc cag cgc atc gtc gat cac gac   288
Asp Ala Gln Leu Arg Arg Ile Trp Arg Gln Arg Ile Val Asp His Asp
                85                  90                  95 ggc gac cat gag ggc gac ggc ggc atc gag cgt tgg ctc aag ctt gcc   336
Gly Asp His Glu Gly Asp Gly Gly Ile Glu Arg Trp Leu Lys Leu Ala
            100                 105                 110 gaa ggc gtc ggc ttc acc cgc gac tac gtg ctc tcg acc aag ggc atc   384
Glu Gly Val Gly Phe Thr Arg Asp Tyr Val Leu Ser Thr Lys Gly Ile
        115                 120                 125 ctg tcg gcg acc cgc ttc tcg gtc gat gcc tat gtc cac ttc gtc tcc   432
Leu Ser Ala Thr Arg Phe Ser Val Asp Ala Tyr Val His Phe Val Ser
    130                 135                 140 gag cgc agc ctg ctc gaa gcc atc gcc tcg tcg ctg acc gag atg ttc   480
Glu Arg Ser Leu Leu Glu Ala Ile Ala Ser Ser Leu Thr Glu Met Phe
145                 150                 155                 160 tcg ccg acg atc atc tcc gag cgc gtc gcc ggg atg ctg aag aac tac   528
```

```
Ser Pro Thr Ile Ile Ser Glu Arg Val Ala Gly Met Leu Lys Asn Tyr
            165                 170                 175 gac ttc atc acc aag gac acg ctg gcc tat ttc gac aag cgc ctg acc       576
Asp Phe Ile Thr Lys Asp Thr Leu Ala Tyr Phe Asp Lys Arg Leu Thr
        180                 185                 190 cag gcc ccg cgc gac gcc gat ttc gcc ctc gac tac gtc aag cgg cac       624
Gln Ala Pro Arg Asp Ala Asp Phe Ala Leu Asp Tyr Val Lys Arg His
    195                 200                 205 gcc acc acg cct gag atg cag cgg gcg gcg ata gat gcg ttg acg ttc       672
Ala Thr Thr Pro Glu Met Gln Arg Ala Ala Ile Asp Ala Leu Thr Phe
210                 215                 220 aag tgc aac gtg ctc tgg acg caa ctc gat gcg ctc tac ttc gcc tat       720
Lys Cys Asn Val Leu Trp Thr Gln Leu Asp Ala Leu Tyr Phe Ala Tyr
225                 230                 235                 240 gtc gcc ccc ggc atg gtg ccg ccg gat gct tgg cag ccg ggc gag ggc       768
Val Ala Pro Gly Met Val Pro Pro Asp Ala Trp Gln Pro Gly Glu Gly
                245                 250                 255 ctt gtt gcc gag acg aac tcc gcc gag gac agc ccc gcc gct gcg gcc       816
Leu Val Ala Glu Thr Asn Ser Ala Glu Asp Ser Pro Ala Ala Ala Ala
            260                 265                 270 agc ccc gcc gcg acg aca gct gaa ccc acg gcc ttc tcg ggc agt gac       864
Ser Pro Ala Ala Thr Thr Ala Glu Pro Thr Ala Phe Ser Gly Ser Asp
        275                 280                 285 gtg ccg cgc ctg ccc cgc ggc gtg cgc ctg cgc ttc gac gag gtc cgc       912
Val Pro Arg Leu Pro Arg Gly Val Arg Leu Arg Phe Asp Glu Val Arg
    290                 295                 300 aac aag cac gtg ctg ctc gcc ccc gag cgc acc ttc gac ctc gac gac       960
Asn Lys His Val Leu Leu Ala Pro Glu Arg Thr Phe Asp Leu Asp Asp
305                 310                 315                 320 aac gcc gtc gcg gtc ctc aag ctc gtc gat ggc cgg aac acg gtt tcg      1008
Asn Ala Val Ala Val Leu Lys Leu Val Asp Gly Arg Asn Thr Val Ser
                325                 330                 335 cag atc gcc cag att ctg ggt cag acc tac gac gcc gac ccg gcc atc      1056
Gln Ile Ala Gln Ile Leu Gly Gln Thr Tyr Asp Ala Asp Pro Ala Ile
            340                 345                 350 atc gaa gcc gac atc ctc ccg atg ctg gcc ggc ctc gcg caa aaa agg      1104
Ile Glu Ala Asp Ile Leu Pro Met Leu Ala Gly Leu Ala Gln Lys Arg
        355                 360                 365 gtt ctg gag cga tga                                                   1119
Val Leu Glu Arg
    370
```

<210> SEQ ID NO 6
<211> LENGTH: 372
<212> TYPE: PRT
<213> ORGANISM: Methylobacterium extorquens

<400> SEQUENCE: 6

```
Met Thr Ala Gln Phe Pro Pro Val Pro Asp Thr Glu Gln Arg Leu
1               5                   10                  15

Leu Ser His Glu Glu Leu Glu Ala Ala Leu Arg Asp Ile Gly Ala Arg
            20                  25                  30

Arg Tyr His Asn Leu His Pro Phe His Arg Leu Leu His Asp Gly Lys
        35                  40                  45

Leu Ser Lys Asp Gln Val Arg Ala Trp Ala Leu Asn Arg Tyr Tyr Tyr
    50                  55                  60

Gln Ala Met Ile Pro Val Lys Asp Ala Ala Leu Leu Ala Arg Leu Pro
65                  70                  75                  80

Asp Ala Gln Leu Arg Arg Ile Trp Arg Gln Arg Ile Val Asp His Asp
```

```
            85                  90                  95
Gly Asp His Glu Gly Asp Gly Ile Glu Arg Trp Leu Lys Leu Ala
            100                 105                 110

Glu Gly Val Gly Phe Thr Arg Asp Tyr Val Leu Ser Thr Lys Gly Ile
            115                 120                 125

Leu Ser Ala Thr Arg Phe Ser Val Asp Ala Tyr Val His Phe Val Ser
130                 135                 140

Glu Arg Ser Leu Leu Glu Ala Ile Ala Ser Ser Leu Thr Glu Met Phe
145                 150                 155                 160

Ser Pro Thr Ile Ile Ser Glu Arg Val Ala Gly Met Leu Lys Asn Tyr
                165                 170                 175

Asp Phe Ile Thr Lys Asp Thr Leu Ala Tyr Phe Asp Lys Arg Leu Thr
                180                 185                 190

Gln Ala Pro Arg Asp Ala Asp Phe Ala Leu Asp Tyr Val Lys Arg His
                195                 200                 205

Ala Thr Thr Pro Glu Met Gln Arg Ala Ala Ile Asp Ala Leu Thr Phe
            210                 215                 220

Lys Cys Asn Val Leu Trp Thr Gln Leu Asp Ala Leu Tyr Phe Ala Tyr
225                 230                 235                 240

Val Ala Pro Gly Met Val Pro Pro Asp Ala Trp Gln Pro Gly Glu Gly
                245                 250                 255

Leu Val Ala Glu Thr Asn Ser Ala Glu Asp Ser Pro Ala Ala Ala
                260                 265                 270

Ser Pro Ala Ala Thr Thr Ala Glu Pro Thr Ala Phe Ser Gly Ser Asp
            275                 280                 285

Val Pro Arg Leu Pro Arg Gly Val Arg Leu Arg Phe Asp Glu Val Arg
            290                 295                 300

Asn Lys His Val Leu Leu Ala Pro Glu Arg Thr Phe Asp Leu Asp Asp
305                 310                 315                 320

Asn Ala Val Ala Val Leu Lys Leu Val Asp Gly Arg Asn Thr Val Ser
                325                 330                 335

Gln Ile Ala Gln Ile Leu Gly Gln Thr Tyr Asp Ala Asp Pro Ala Ile
                340                 345                 350

Ile Glu Ala Asp Ile Leu Pro Met Leu Ala Gly Leu Ala Gln Lys Arg
            355                 360                 365

Val Leu Glu Arg
    370

<210> SEQ ID NO 7
<211> LENGTH: 1125
<212> TYPE: DNA
<213> ORGANISM: Methylobacterium extorquens
<220> FEATURE:
<221> NAME/KEY: CDS
<222> LOCATION: (1)..(1125)

<400> SEQUENCE: 7 gtg gac gtc att ccg gcg ccg gtg ggt ctg ctc gcc gag ctg acg cac    48
Val Asp Val Ile Pro Ala Pro Val Gly Leu Leu Ala Glu Leu Thr His
1               5                   10                  15 cgc tgc ccg ctg cgc tgc cca tac tgc tcg aac ccg ctg gag ctc gac    96
Arg Cys Pro Leu Arg Cys Pro Tyr Cys Ser Asn Pro Leu Glu Leu Asp
                20                  25                  30 cgg cgc tcg gcc gag ctg gac acg cag acg tgg ctg cgg gtg ctg acg   144
Arg Arg Ser Ala Glu Leu Asp Thr Gln Thr Trp Leu Arg Val Leu Thr
            35                  40                  45
```

-continued

| | | |
|---|---|---|
| gag gcg gcg ggg ctc ggt gtg ctg cac gtc cac ctg tcg ggc ggt gaa<br>Glu Ala Ala Gly Leu Gly Val Leu His Val His Leu Ser Gly Gly Glu<br>50                         55                       60 | 192 | |
| ccg acc gcc cgc ccc gac atc gtc gag atc acg gcc aaa tgc gcc gaa<br>Pro Thr Ala Arg Pro Asp Ile Val Glu Ile Thr Ala Lys Cys Ala Glu<br>65                         70                       75                   80 | 240 | |
| ctc ggc ctg tac tcg aac ctg atc acc tcc ggc gtc ggc ggt gcc tta<br>Leu Gly Leu Tyr Ser Asn Leu Ile Thr Ser Gly Val Gly Gly Ala Leu<br>                       85                       90                   95 | 288 | |
| gcg aag ctc gac gcg ctc tac gac gtc ggc ctc gac cac gtg cag ctc<br>Ala Lys Leu Asp Ala Leu Tyr Asp Val Gly Leu Asp His Val Gln Leu<br>               100                   105                  110 | 336 | |
| tcc gtc caa ggg gtg gac gcg gcc aac gcg gaa aag atc ggc ggc ctt<br>Ser Val Gln Gly Val Asp Ala Ala Asn Ala Glu Lys Ile Gly Gly Leu<br>          115                   120                  125 | 384 | |
| aag aac gcg cag ccg cag aag atg caa ttc gct gcc cgg gtc acc gaa<br>Lys Asn Ala Gln Pro Gln Lys Met Gln Phe Ala Ala Arg Val Thr Glu<br>130                       135                  140 | 432 | |
| ctc ggc ctg ccg ctg acg ctg aac tcg gtg atc cac cgc ggc aac atc<br>Leu Gly Leu Pro Leu Thr Leu Asn Ser Val Ile His Arg Gly Asn Ile<br>145                     150                  155               160 | 480 | |
| cac gag gtg ccg ggc ttc atc gac ctc gcg gtc aag ctc ggc gcc aag<br>His Glu Val Pro Gly Phe Ile Asp Leu Ala Val Lys Leu Gly Ala Lys<br>               165                   170                  175 | 528 | |
| cgg ctg gag gtg gcc cat acc cag tat tac ggc tgg gcc tat gtg aac<br>Arg Leu Glu Val Ala His Thr Gln Tyr Tyr Gly Trp Ala Tyr Val Asn<br>          180                   185                  190 | 576 | |
| cgc gcc gcg ctg atg ccg gat aag agc cag gtc gac gag tcg atc cgc<br>Arg Ala Ala Leu Met Pro Asp Lys Ser Gln Val Asp Glu Ser Ile Arg<br>               195                   200                  205 | 624 | |
| atc gtc gag gcc gcg cgc gag cgc ctc aag ggt cag ctc gtc atc gac<br>Ile Val Glu Ala Ala Arg Glu Arg Leu Lys Gly Gln Leu Val Ile Asp<br>210                       215                  220 | 672 | |
| ctc gtg gtt ccg gac tac tac gcc aag tac ccg aag gcc tgc gcc ggc<br>Leu Val Val Pro Asp Tyr Tyr Ala Lys Tyr Pro Lys Ala Cys Ala Gly<br>225                     230                  235               240 | 720 | |
| ggc tgg ggc cgc aag ctg atg aac gtg acg ccg cag ggc aag gtg ctg<br>Gly Trp Gly Arg Lys Leu Met Asn Val Thr Pro Gln Gly Lys Val Leu<br>               245                   250                  255 | 768 | |
| ccc tgc cac gcc gca gaa acc atc ccc ggc ctc gaa ttc tgg tac gtc<br>Pro Cys His Ala Ala Glu Thr Ile Pro Gly Leu Glu Phe Trp Tyr Val<br>          260                   265                  270 | 816 | |
| acc gac cac gcg ctc ggc gag atc tgg acg aag tcc ccg gcc ttt gcc<br>Thr Asp His Ala Leu Gly Glu Ile Trp Thr Lys Ser Pro Ala Phe Ala<br>275                       280                  285 | 864 | |
| gcc tat cgc ggc acg tcc tgg atg aag gag ccc tgc cgc tcc tgc gac<br>Ala Tyr Arg Gly Thr Ser Trp Met Lys Glu Pro Cys Arg Ser Cys Asp<br>          290                   295                  300 | 912 | |
| cgg cgc gag aag gat tgg ggc ggg tgc cgc tgc cag gcg ctg gcg ctc<br>Arg Arg Glu Lys Asp Trp Gly Gly Cys Arg Cys Gln Ala Leu Ala Leu<br>305                     310                  315               320 | 960 | |
| acg ggc gac gcg gcc aac acc gat ccg gcc tgc tcc ctt tcg ccg ctg<br>Thr Gly Asp Ala Ala Asn Thr Asp Pro Ala Cys Ser Leu Ser Pro Leu<br>               325                   330                  335 | 1008 | |
| cac gcg aaa atg cgg gat ctt gcc aag gaa gag gct gcc gag acc ccg<br>His Ala Lys Met Arg Asp Leu Ala Lys Glu Glu Ala Ala Glu Thr Pro<br>          340                   345                  350 | 1056 | |
| ccc gat tat ata tac cgc agc atc ggg acg aat gtg caa aac ccg ttg<br>Pro Asp Tyr Ile Tyr Arg Ser Ile Gly Thr Asn Val Gln Asn Pro Leu<br>               355                   360                  365 | 1104 | |

```
agc gaa aag gca ccc ctt tga                                              1125
Ser Glu Lys Ala Pro Leu
    370
```

<210> SEQ ID NO 8
<211> LENGTH: 374
<212> TYPE: PRT
<213> ORGANISM: Methylobacterium extorquens

<400> SEQUENCE: 8

```
Val Asp Val Ile Pro Ala Pro Val Gly Leu Leu Ala Glu Leu Thr His
1               5                   10                  15

Arg Cys Pro Leu Arg Cys Pro Tyr Cys Ser Asn Pro Leu Glu Leu Asp
            20                  25                  30

Arg Arg Ser Ala Glu Leu Asp Thr Gln Thr Trp Leu Arg Val Leu Thr
        35                  40                  45

Glu Ala Ala Gly Leu Gly Val Leu His Val His Leu Ser Gly Gly Glu
    50                  55                  60

Pro Thr Ala Arg Pro Asp Ile Val Glu Ile Thr Ala Lys Cys Ala Glu
65                  70                  75                  80

Leu Gly Leu Tyr Ser Asn Leu Ile Thr Ser Gly Val Gly Gly Ala Leu
                85                  90                  95

Ala Lys Leu Asp Ala Leu Tyr Asp Val Gly Leu Asp His Val Gln Leu
            100                 105                 110

Ser Val Gln Gly Val Asp Ala Ala Asn Ala Glu Lys Ile Gly Gly Leu
        115                 120                 125

Lys Asn Ala Gln Pro Gln Lys Met Gln Phe Ala Ala Arg Val Thr Glu
    130                 135                 140

Leu Gly Leu Pro Leu Thr Leu Asn Ser Val Ile His Arg Gly Asn Ile
145                 150                 155                 160

His Glu Val Pro Gly Phe Ile Asp Leu Ala Val Lys Leu Gly Ala Lys
                165                 170                 175

Arg Leu Glu Val Ala His Thr Gln Tyr Tyr Gly Trp Ala Tyr Val Asn
            180                 185                 190

Arg Ala Ala Leu Met Pro Asp Lys Ser Gln Val Asp Glu Ser Ile Arg
        195                 200                 205

Ile Val Glu Ala Ala Arg Glu Arg Leu Lys Gly Gln Leu Val Ile Asp
    210                 215                 220

Leu Val Val Pro Asp Tyr Tyr Ala Lys Tyr Pro Lys Ala Cys Ala Gly
225                 230                 235                 240

Gly Trp Gly Arg Lys Leu Met Asn Val Thr Pro Gln Gly Lys Val Leu
                245                 250                 255

Pro Cys His Ala Ala Glu Thr Ile Pro Gly Leu Glu Phe Trp Tyr Val
            260                 265                 270

Thr Asp His Ala Leu Gly Glu Ile Trp Thr Lys Ser Pro Ala Phe Ala
        275                 280                 285

Ala Tyr Arg Gly Thr Ser Trp Met Lys Glu Pro Cys Arg Ser Cys Asp
    290                 295                 300

Arg Arg Glu Lys Asp Trp Gly Gly Cys Arg Cys Gln Ala Leu Ala Leu
305                 310                 315                 320

Thr Gly Asp Ala Ala Asn Thr Asp Pro Ala Cys Ser Leu Ser Pro Leu
                325                 330                 335

His Ala Lys Met Arg Asp Leu Ala Lys Glu Ala Ala Glu Thr Pro
            340                 345                 350
```

Pro Asp Tyr Ile Tyr Arg Ser Ile Gly Thr Asn Val Gln Asn Pro Leu
    355                 360                 365

Ser Glu Lys Ala Pro Leu
    370

<210> SEQ ID NO 9
<211> LENGTH: 3473
<212> TYPE: DNA
<213> ORGANISM: Methylobacterium extorquens

<400> SEQUENCE: 9

```
atgaagtggg ctgcccccat cgtttccgag atctgcgtcg gcatggaagt cacgagctac      60
gagtcggccg agatcgacac cttcaactaa ggtgatttga gccgggttgg ggttgcaggc     120
atcagcgggt tttcaccatg catgtcgtaa tcctgggctc ggctgcgggc ggcggcgttc     180
ctcaatggaa ctgccgctgc tccatctgct ccctggcctg ggcgggcgat tcccgcgtca     240
ggccgcgcac gcagtcgagc atcgcagtct ctcctgacgg gaacgctgg ctcctgctga      300
acgcctctcc cgatatccgt cagcagatcc aggccaatcc gcagatgcat ccgcgcgagg     360
gcctgcgcca ctcgccgatc cacgcggtgc tgctgacgaa cggcgacgtc gatcacgttg     420
cgggcctgct gaccctgcgc gagggccagc ccttcacgct ctacgcgaca cccggcatcc     480
tggcctccgt ctccgacaac cgcgtcttcg acgtgatggc cgccgacgtg gtgaagcggc     540
agacgatcgc cctcaacgag accttcgagc cggtgcccgg cctctcggtg acgctgttct     600
ccgtccccgg caaggtgccg ctctggctgg agacgcctc gatggagatc ggggcggaga      660
ccgaaaccac ggtcggcacg atgatcgagg cggggggcaa gcgcctcgcc tacatccccg     720
gctgcgcccg ggtgacggag gatctcaaag cccgcatcgc cggcgcagac gcgctcctgt     780
cgacggcac ggtgctggag gacgacgaca tgatccgcgc cggtgtcggc accaagaccg      840
gctggcgcat gggccatatc cagatgaacg cgagaccgg ctcgatcgcg tctctcgccg      900
atatcgagat cggccgacgg gtcttcgttc acatcaacaa caccaatccg gtcctgatcg     960
aggattcgta cgagcgcgcg agcgtcgagg cgcgcggctg gaccgtcgcc catgacggcc    1020
tgaccctcga tctctgatca ggctgatgtc ttgggaagag cccggtctgg aaatttagtg    1080
ccggactgaa tatgttttgc acgatccaat cgtgcggcag cggccctgcc ccgatcggta    1140
ccgggcccca tttaaaaata aatccaggaa acgcgactcg aagctcgggg gaaaccgaac    1200
gccatgaccg cccaattccc gccgcccgtc ccggacaccg agcaacgcct gctgagccac    1260
gaggagcttg aggcggcgct ccgcgatatc ggtgcacggc gctaccacaa cctccacccg    1320
ttccaccggc tgctgcacga cggcaagctg tcgaaggatc aggtccgggc ctgggcgctc    1380
aaccgctact attatcaggc gatgattccg gtgaaggatg cagcgctgct ggctcgcctg    1440
ccggatgcgc agcttcgccg aatctggcgc cagcgcatcg tcgatcacga cggcgaccat    1500
gagggcgacg gcggcatcga gcgttggctc aagcttgccg aaggcgtcgg cttcacccgc    1560
gactacgtgc tctcgaccaa gggcatcctg tcggcgaccc gcttctcggt cgatgcctat    1620
gtccacttcg tctccgagcg cagcctgctc gaagccatcg cctcctcgct gaccgagatg    1680
ttctcgccga cgatcatctc cgagcgcgtc gccgggatgt gaagaactac gacttcatc     1740
accaaggaca cgctggccta tttcgacaag cgcctgaccc aggccccgcg cgacgccgat    1800
ttcgccctcg actacgtcaa gcggcacgcc accacgcctg agatgcagcg gcggcgata     1860
gatgcgttga cgttcaagtg caacgtgctc tggacgcaac tcgatgcgct ctacttcgcc    1920
tatgtcgccc ccggcatggt gccgccggat gcttggcagc cgggcgaggg ccttgttgcc    1980
```

```
gagacgaact ccgccgagga cagccccgcc gctgcggcca gccccgccgc gacgacagct    2040
gaacccacgg ccttctcggg cagtgacgtg ccgcgcctgc ccgcggcgt gcgcctgcgc     2100 ttcgacgagg tccgcaacaa gcacgtgctg ctcgcccccg agcgcacctt cgacctcgac    2160
gacaacgccg tcgcggtcct caagctcgtc gatggccgga acacggtttc gcagatcgcc    2220
cagattctgg gtcagaccta cgacgccgac ccggccatca tcgaagccga catcctcccg    2280
atgctggccg gcctcgcgca aaaagggtt ctggagcgat gaatgcaccg acacccgccc     2340
cctcccccgt ggacgtcatt ccggcgccgg tgggtctgct cgccgagctg acgcaccgct    2400
gcccgctgcg ctgcccatac tgctcgaacc cgctggagct cgaccggcgc tcggccgagc    2460
tggacacgca gacgtggctg cgggtgctga cggaggcggc ggggctcggt gtgctgcacg    2520
tccacctgtc gggcggtgaa ccgaccgccc gccccgacat cgtcgagatc acggccaaat    2580
gcgccgaact cggcctgtac tcgaacctga tcacctccgg cgtcggcggt gccttagcga    2640
agctcgacgc gctctacgac gtcggcctcg accacgtgca gctctccgtc caaggggtgg    2700
acgcggccaa cgcggaaaag atcggcggcc ttaagaacgc gcagccgcag aagatgcaat    2760
tcgctgcccg ggtcaccgaa ctcggcctgc cgctgacgct gaactcggtg atccaccgcg    2820
gcaacatcca cgaggtgccg ggcttcatcg acctcgcggt caagctcggc gccaagcggc    2880
tggaggtggc ccatacccag tattacggct gggcctatgt gaaccgcgcc gcgctgatgc    2940
cggataagag ccaggtcgac gagtcgatcc gcatcgtcga ggccgcgcgc gagcgcctca    3000
agggtcagct cgtcatcgac ctcgtggttc cggactacta cgccaagtac ccgaaggcct    3060
gcgccggcgg ctggggccgc aagctgatga acgtgacgcc gcagggcaag gtgctgccct    3120
gccacgccgc agaaaccatc cccggcctcg aattctggta cgtcaccgac cacgcgctcg    3180
gcgagatctg gacgaagtcc ccggcctttg ccgcctatcg cggcacgtcc tggatgaagg    3240
agccctgccg ctcctgcgac cggcgcgaga aggattgggg cggtgccgc tgccaggcgc     3300 tggcgctcac gggcgacgcg gccaacaccg atccggcctg ctcccttcg ccgctgcacg     3360 cgaaaatgcg ggatcttgcc aaggaagagg ctgccgagac cccgcccgat tatatatacc    3420
gcagcatcgg gacgaatgtg caaaacccgt tgagcgaaaa ggcaccccctt tga          3473
```

<210> SEQ ID NO 10
<211> LENGTH: 90
<212> TYPE: DNA
<213> ORGANISM: Methylobacterium extorquens
<220> FEATURE:
<221> NAME/KEY: CDS
<222> LOCATION: (1)..(90)

<400> SEQUENCE: 10

```
atg aag tgg tct gcc ccc atc gtt gcc gag atc tgc gtc ggc atg gaa     48
Met Lys Trp Ser Ala Pro Ile Val Ala Glu Ile Cys Val Gly Met Glu
1               5                   10                  15 gtc acc tcc tac gag tcc gcc gag atc gac acc ttc aac taa             90
Val Thr Ser Tyr Glu Ser Ala Glu Ile Asp Thr Phe Asn
            20                  25
```

<210> SEQ ID NO 11
<211> LENGTH: 29
<212> TYPE: PRT
<213> ORGANISM: Methylobacterium extorquens

<400> SEQUENCE: 11

Met Lys Trp Ser Ala Pro Ile Val Ala Glu Ile Cys Val Gly Met Glu

<210> SEQ ID NO 12
<211> LENGTH: 90
<212> TYPE: DNA
<213> ORGANISM: Methylobacterium extorquens
<220> FEATURE:
<221> NAME/KEY: CDS
<222> LOCATION: (1)..(90)

<400> SEQUENCE: 12

```
atg aag tgg tcc gct ccc gtc gtt gcc gag atc tgt gtc ggc atg gaa    48
Met Lys Trp Ser Ala Pro Val Val Ala Glu Ile Cys Val Gly Met Glu
1               5                   10                  15 gtc acc tcc tac gag tcc gct gag atc gac acc ttc aac taa            90
Val Thr Ser Tyr Glu Ser Ala Glu Ile Asp Thr Phe Asn
            20                  25
```

<210> SEQ ID NO 13
<211> LENGTH: 29
<212> TYPE: PRT
<213> ORGANISM: Methylobacterium extorquens

<400> SEQUENCE: 13

```
Met Lys Trp Ser Ala Pro Val Val Ala Glu Ile Cys Val Gly Met Glu
1               5                   10                  15

Val Thr Ser Tyr Glu Ser Ala Glu Ile Asp Thr Phe Asn
            20                  25
```

<210> SEQ ID NO 14
<211> LENGTH: 123
<212> TYPE: DNA
<213> ORGANISM: Hyphomicrobium denitrificans
<220> FEATURE:
<221> NAME/KEY: CDS
<222> LOCATION: (1)..(123)

<400> SEQUENCE: 14

```
atg gaa agc agt tac cgc ttt gga gga acc aca atg aaa atc tgg acg    48
Met Glu Ser Ser Tyr Arg Phe Gly Gly Thr Thr Met Lys Ile Trp Thr
1               5                   10                  15 aag ccc gct gtg cgc gag cag gaa gtt ggt ctc gaa gtg acg agc tac    96
Lys Pro Ala Val Arg Glu Gln Glu Val Gly Leu Glu Val Thr Ser Tyr
            20                  25                  30 ctg ccg gct gaa atc gac ctc atc tga                                123
Leu Pro Ala Glu Ile Asp Leu Ile
            35                  40
```

<210> SEQ ID NO 15
<211> LENGTH: 40
<212> TYPE: PRT
<213> ORGANISM: Hyphomicrobium denitrificans

<400> SEQUENCE: 15

```
Met Glu Ser Ser Tyr Arg Phe Gly Gly Thr Thr Met Lys Ile Trp Thr
1               5                   10                  15

Lys Pro Ala Val Arg Glu Gln Glu Val Gly Leu Glu Val Thr Ser Tyr
            20                  25                  30

Leu Pro Ala Glu Ile Asp Leu Ile
            35                  40
```

```
<210> SEQ ID NO 16
<211> LENGTH: 933
<212> TYPE: DNA
<213> ORGANISM: Hyphomicrobium denitrificans
<220> FEATURE:
<221> NAME/KEY: CDS
<222> LOCATION: (1)..(933)

<400> SEQUENCE: 16
```

| | | | | | | | | | | | | | | | | |
|---|---|---|---|---|---|---|---|---|---|---|---|---|---|---|---|---|
| atg | atc | ata | aaa | gtg | ctc | ggg | tcc | tcc | gct | ggg | ggt | gga | ttc | ccg | cag | 48 |
| Met | Ile | Ile | Lys | Val | Leu | Gly | Ser | Ser | Ala | Gly | Gly | Gly | Phe | Pro | Gln | |
| 1 | | | | 5 | | | | | 10 | | | | | 15 | | |
| tgg | aac | tgc | aat | ggc | atg | cag | tcg | gca | aag | gtt | cgc | tca | ggc | gct | gcc | 96 |
| Trp | Asn | Cys | Asn | Gly | Met | Gln | Ser | Ala | Lys | Val | Arg | Ser | Gly | Ala | Ala | |
| | | | 20 | | | | | 25 | | | | | 30 | | | |
| ggg | ttt | aag | gcg | cgc | ttg | caa | tcg | tcc | ctt | gcc | gct | tcg | agc | gac | ggc | 144 |
| Gly | Phe | Lys | Ala | Arg | Leu | Gln | Ser | Ser | Leu | Ala | Ala | Ser | Ser | Asp | Gly | |
| | | 35 | | | | | 40 | | | | | 45 | | | | |
| aag | aat | tgg | gtg | ttg | ctc | aac | gcc | tcg | ccc | gac | att | cgc | cag | cag | atc | 192 |
| Lys | Asn | Trp | Val | Leu | Leu | Asn | Ala | Ser | Pro | Asp | Ile | Arg | Gln | Gln | Ile | |
| 50 | | | | | 55 | | | | | 60 | | | | | | |
| aac | gag | acg | ccc | gag | ttg | cac | cct | gaa | acg | acg | ggc | gca | aag | cgt | aat | 240 |
| Asn | Glu | Thr | Pro | Glu | Leu | His | Pro | Glu | Thr | Thr | Gly | Ala | Lys | Arg | Asn | |
| 65 | | | | | 70 | | | | | 75 | | | | | 80 | |
| tcg | ccg | atc | aag | gcc | gtt | gtc | gtc | acc | aat | gcc | gac | gtc | gat | cac | atc | 288 |
| Ser | Pro | Ile | Lys | Ala | Val | Val | Val | Thr | Asn | Ala | Asp | Val | Asp | His | Ile | |
| | | | | 85 | | | | | 90 | | | | | 95 | | |
| atc | gga | ctg | atc | ggc | ctc | cgc | gaa | ggt | cag | ccg | ttt | tcg | atc | tac | ggt | 336 |
| Ile | Gly | Leu | Ile | Gly | Leu | Arg | Glu | Gly | Gln | Pro | Phe | Ser | Ile | Tyr | Gly | |
| | | | 100 | | | | | 105 | | | | | 110 | | | |
| tcc | gac | ctc | gtc | ctc | gcg | acg | ctg | aag | gca | aat | tca | gtt | ttc | aac | gtc | 384 |
| Ser | Asp | Leu | Val | Leu | Ala | Thr | Leu | Lys | Ala | Asn | Ser | Val | Phe | Asn | Val | |
| | | 115 | | | | | 120 | | | | | 125 | | | | |
| tgc | aac | ccc | gag | atc | gta | ccg | cgc | ttg | gaa | ctg | ccc | ttc | gac | agg | ccg | 432 |
| Cys | Asn | Pro | Glu | Ile | Val | Pro | Arg | Leu | Glu | Leu | Pro | Phe | Asp | Arg | Pro | |
| 130 | | | | | 135 | | | | | 140 | | | | | | |
| acc | gaa | ctg | cat | ggc | gcc | ggc | gtc | gac | ctc | gga | ctg | acg | gtc | gaa | gcc | 480 |
| Thr | Glu | Leu | His | Gly | Ala | Gly | Val | Asp | Leu | Gly | Leu | Thr | Val | Glu | Ala | |
| 145 | | | | | 150 | | | | | 155 | | | | | 160 | |
| ttc | cct | gtc | cca | ggc | aag | gtt | gcg | ctc | ttt | ctg | gag | aag | ggc | ggc | gcc | 528 |
| Phe | Pro | Val | Pro | Gly | Lys | Val | Ala | Leu | Phe | Leu | Glu | Lys | Gly | Gly | Ala | |
| | | | | 165 | | | | | 170 | | | | | 175 | | |
| aac | gaa | aat | tac | ggc | agc | cgc | gac | ggc | gac | acc | atc | ggc | ttg | aaa | gtg | 576 |
| Asn | Glu | Asn | Tyr | Gly | Ser | Arg | Asp | Gly | Asp | Thr | Ile | Gly | Leu | Lys | Val | |
| | | | 180 | | | | | 185 | | | | | 190 | | | |
| acg | gat | cgt | aaa | gcc | ggc | aag | tcg | ttt | ttc | tac | att | ccc | ggc | tgc | gcc | 624 |
| Thr | Asp | Arg | Lys | Ala | Gly | Lys | Ser | Phe | Phe | Tyr | Ile | Pro | Gly | Cys | Ala | |
| | | 195 | | | | | 200 | | | | | 205 | | | | |
| gaa | gtc | gac | gcg | ccg | ctc | gcc | gat | cgc | atc | cgc | gga | gcc | gat | gtc | att | 672 |
| Glu | Val | Asp | Ala | Pro | Leu | Ala | Asp | Arg | Ile | Arg | Gly | Ala | Asp | Val | Ile | |
| 210 | | | | | 215 | | | | | 220 | | | | | | |
| ttc | ttc | gac | ggc | acg | ctt | tac | gaa | gac | ggc | gaa | atg | atc | gct | caa | gga | 720 |
| Phe | Phe | Asp | Gly | Thr | Leu | Tyr | Glu | Asp | Gly | Glu | Met | Ile | Ala | Gln | Gly | |
| 225 | | | | | 230 | | | | | 235 | | | | | 240 | |
| ttg | ttg | aac | aag | acc | ggc | aag | cga | atg | ggc | cat | att | tcg | gtc | tcc | ggt | 768 |
| Leu | Leu | Asn | Lys | Thr | Gly | Lys | Arg | Met | Gly | His | Ile | Ser | Val | Ser | Gly | |
| | | | | 245 | | | | | 250 | | | | | 255 | | |
| cac | gaa | ggc | tct | atc | gcg | gct | ttg | agc | cat | ctc | aac | gtt | cgc | cga | aaa | 816 |
| His | Glu | Gly | Ser | Ile | Ala | Ala | Leu | Ser | His | Leu | Asn | Val | Arg | Arg | Lys | |
| | | | 260 | | | | | 265 | | | | | 270 | | | |
| att | tac | gtt | cac | atc | aac | aat | tca | aac | ccg | atc | ctg | gat | gaa | aat | tcg | 864 |
| | | | | | | | | | | | | | | | | |

```
                Ile Tyr Val His Ile Asn Asn Ser Asn Pro Ile Leu Asp Glu Asn Ser
                            275                 280                 285 gaa gct cga aaa gct gtt gaa aca gcc ggg tgg gag gtt ggt ttt gat          912
Glu Ala Arg Lys Ala Val Glu Thr Ala Gly Trp Glu Val Gly Phe Asp
        290                 295                 300 gga atg gag gtc cgc tta tga                                              933
Gly Met Glu Val Arg Leu
305                 310
```

<210> SEQ ID NO 17
<211> LENGTH: 310
<212> TYPE: PRT
<213> ORGANISM: Hyphomicrobium denitrificans

<400> SEQUENCE: 17

```
Met Ile Ile Lys Val Leu Gly Ser Ser Ala Gly Gly Phe Pro Gln
1               5                   10                  15

Trp Asn Cys Asn Gly Met Gln Ser Ala Lys Val Arg Ser Gly Ala Ala
                20                  25                  30

Gly Phe Lys Ala Arg Leu Gln Ser Ser Leu Ala Ala Ser Ser Asp Gly
            35                  40                  45

Lys Asn Trp Val Leu Leu Asn Ala Ser Pro Asp Ile Arg Gln Gln Ile
50                  55                  60

Asn Glu Thr Pro Glu Leu His Pro Glu Thr Thr Gly Ala Lys Arg Asn
65                  70                  75                  80

Ser Pro Ile Lys Ala Val Val Thr Asn Ala Asp Val Asp His Ile
                85                  90                  95

Ile Gly Leu Ile Gly Leu Arg Glu Gly Gln Pro Phe Ser Ile Tyr Gly
            100                 105                 110

Ser Asp Leu Val Leu Ala Thr Leu Lys Ala Asn Ser Val Phe Asn Val
        115                 120                 125

Cys Asn Pro Glu Ile Val Pro Arg Leu Glu Leu Pro Phe Asp Arg Pro
    130                 135                 140

Thr Glu Leu His Gly Ala Gly Val Asp Leu Gly Leu Thr Val Glu Ala
145                 150                 155                 160

Phe Pro Val Pro Gly Lys Val Ala Leu Phe Leu Glu Lys Gly Gly Ala
                165                 170                 175

Asn Glu Asn Tyr Gly Ser Arg Asp Gly Asp Thr Ile Gly Leu Lys Val
            180                 185                 190

Thr Asp Arg Lys Ala Gly Lys Ser Phe Phe Tyr Ile Pro Gly Cys Ala
        195                 200                 205

Glu Val Asp Ala Pro Leu Ala Asp Arg Ile Arg Gly Ala Asp Val Ile
    210                 215                 220

Phe Phe Asp Gly Thr Leu Tyr Glu Asp Gly Glu Met Ile Ala Gln Gly
225                 230                 235                 240

Leu Leu Asn Lys Thr Gly Lys Arg Met Gly His Ile Ser Val Ser Gly
                245                 250                 255

His Glu Gly Ser Ile Ala Ala Leu Ser His Leu Asn Val Arg Arg Lys
            260                 265                 270

Ile Tyr Val His Ile Asn Asn Ser Asn Pro Ile Leu Asp Glu Asn Ser
        275                 280                 285

Glu Ala Arg Lys Ala Val Glu Thr Ala Gly Trp Glu Val Gly Phe Asp
    290                 295                 300

Gly Met Glu Val Arg Leu
305                 310
```

<210> SEQ ID NO 18
<211> LENGTH: 777
<212> TYPE: DNA
<213> ORGANISM: Hyphomicrobium denitrificans
<220> FEATURE:
<221> NAME/KEY: CDS
<222> LOCATION: (1)..(777)

<400> SEQUENCE: 18

```
atg aac ccg gtc agc gtt gga aag aaa tta gca gag ctt cgc ggt gac    48
Met Asn Pro Val Ser Val Gly Lys Lys Leu Ala Glu Leu Arg Gly Asp
1               5                   10                  15 gag gcg ccg atg ccg gtc gcc gaa ttc gaa gca gcc att cgt gcg gtc    96
Glu Ala Pro Met Pro Val Ala Glu Phe Glu Ala Ala Ile Arg Ala Val
            20                  25                  30 gga ccc gag cgc tac cat gac ctg cat ccc ttc cat cac atg ctt cac   144
Gly Pro Glu Arg Tyr His Asp Leu His Pro Phe His His Met Leu His
        35                  40                  45 ggc ggc aag ctg aac aag gga cag gtg cag gcc tgg gcg ctc aat cgc   192
Gly Gly Lys Leu Asn Lys Gly Gln Val Gln Ala Trp Ala Leu Asn Arg
50                  55                  60 ttc tgc tat cag tcc gcc gtt ccg cgc aag gat gca gcg ctc atc agc   240
Phe Cys Tyr Gln Ser Ala Val Pro Arg Lys Asp Ala Ala Leu Ile Ser
65                  70                  75                  80 cgg gtt tac gat cgc gag ctt cgc cgc gag tgg acg cat cgc att ctc   288
Arg Val Tyr Asp Arg Glu Leu Arg Arg Glu Trp Thr His Arg Ile Leu
                85                  90                  95 gat cat gat ggt ctg ctt cct gat gaa gaa ggc ggc atc gag cgt tgg   336
Asp His Asp Gly Leu Leu Pro Asp Glu Glu Gly Gly Ile Glu Arg Trp
            100                 105                 110 ctc gtg ctg acg gac ggc ctt gga ctc gat cgc gag tac gtc atc tcg   384
Leu Val Leu Thr Asp Gly Leu Gly Leu Asp Arg Glu Tyr Val Ile Ser
        115                 120                 125 cgg cgc ggc gcg ctt ccg gcg acc gtc ttt gcc gtc gag gct tac gtc   432
Arg Arg Gly Ala Leu Pro Ala Thr Val Phe Ala Val Glu Ala Tyr Val
    130                 135                 140 acg ttc gtg cgc gag cag cca ttg acg atc gcc gtc gcc tcc tcg ctg   480
Thr Phe Val Arg Glu Gln Pro Leu Thr Ile Ala Val Ala Ser Ser Leu
145                 150                 155                 160 acc gag ctg ttc gcg ccg aag att cac aaa gaa cgc atc gcc ggc atg   528
Thr Glu Leu Phe Ala Pro Lys Ile His Lys Glu Arg Ile Ala Gly Met
                165                 170                 175 ctc gag aac tac aac ttc atc gac gac aag gtg atg gcg tat ttc aaa   576
Leu Glu Asn Tyr Asn Phe Ile Asp Asp Lys Val Met Ala Tyr Phe Lys
            180                 185                 190 cgc cgc ctg acg cag gct ccg cgc gac gcc gat ttc gca ctg aac tac   624
Arg Arg Leu Thr Gln Ala Pro Arg Asp Ala Asp Phe Ala Leu Asn Tyr
        195                 200                 205 ata ctc gag aac gcc cgc acg cgc gac gaa cag caa gcc tgc atc gac   672
Ile Leu Glu Asn Ala Arg Thr Arg Asp Glu Gln Gln Ala Cys Ile Asp
    210                 215                 220 gcg gtg cgc ttc aaa tgc aat gtt ctc tgg gtg cag ctc gac gcg ctc   720
Ala Val Arg Phe Lys Cys Asn Val Leu Trp Val Gln Leu Asp Ala Leu
225                 230                 235                 240 tac cac gct tac gtc gac gga cac att cct ccg gga gct ttc cgg ccg   768
Tyr His Ala Tyr Val Asp Gly His Ile Pro Pro Gly Ala Phe Arg Pro
                245                 250                 255 gag aat taa                                                        777
Glu Asn
```

-continued

```
<210> SEQ ID NO 19
<211> LENGTH: 258
<212> TYPE: PRT
<213> ORGANISM: Hyphomicrobium denitrificans

<400> SEQUENCE: 19
```

Met Asn Pro Val Ser Val Gly Lys Lys Leu Ala Glu Leu Arg Gly Asp
1               5                   10                  15

Glu Ala Pro Met Pro Val Ala Glu Phe Glu Ala Ala Ile Arg Ala Val
            20                  25                  30

Gly Pro Glu Arg Tyr His Asp Leu His Pro Phe His His Met Leu His
        35                  40                  45

Gly Gly Lys Leu Asn Lys Gly Gln Val Gln Ala Trp Ala Leu Asn Arg
    50                  55                  60

Phe Cys Tyr Gln Ser Ala Val Pro Arg Lys Asp Ala Ala Leu Ile Ser
65                  70                  75                  80

Arg Val Tyr Asp Arg Glu Leu Arg Arg Glu Trp Thr His Arg Ile Leu
                85                  90                  95

Asp His Asp Gly Leu Leu Pro Asp Glu Gly Gly Ile Glu Arg Trp
            100                 105                 110

Leu Val Leu Thr Asp Gly Leu Gly Leu Asp Arg Glu Tyr Val Ile Ser
        115                 120                 125

Arg Arg Gly Ala Leu Pro Ala Thr Val Phe Ala Val Glu Ala Tyr Val
    130                 135                 140

Thr Phe Val Arg Glu Gln Pro Leu Thr Ile Ala Val Ala Ser Ser Leu
145                 150                 155                 160

Thr Glu Leu Phe Ala Pro Lys Ile His Lys Glu Arg Ile Ala Gly Met
                165                 170                 175

Leu Glu Asn Tyr Asn Phe Ile Asp Asp Lys Val Met Ala Tyr Phe Lys
            180                 185                 190

Arg Arg Leu Thr Gln Ala Pro Arg Asp Ala Asp Phe Ala Leu Asn Tyr
        195                 200                 205

Ile Leu Glu Asn Ala Arg Thr Arg Asp Glu Gln Gln Ala Cys Ile Asp
    210                 215                 220

Ala Val Arg Phe Lys Cys Asn Val Leu Trp Val Gln Leu Asp Ala Leu
225                 230                 235                 240

Tyr His Ala Tyr Val Asp Gly His Ile Pro Pro Gly Ala Phe Arg Pro
                245                 250                 255

Glu Asn

```
<210> SEQ ID NO 20
<211> LENGTH: 303
<212> TYPE: DNA
<213> ORGANISM: Hyphomicrobium denitrificans
<220> FEATURE:
<221> NAME/KEY: CDS
<222> LOCATION: (1)..(303)

<400> SEQUENCE: 20
``` atg aac gca gac gca ccg cgt acg aga acg atg gtc gtc ccg gct tcc     48
Met Asn Ala Asp Ala Pro Arg Thr Arg Thr Met Val Val Pro Ala Ser
1               5                   10                  15 aag ccg gga ctg ccg acg cac atc aag ctg cgc cac gac gcc ggc cgc     96
Lys Pro Gly Leu Pro Thr His Ile Lys Leu Arg His Asp Ala Gly Arg
            20                  25                  30 ggc cga tgg cac gtg ctt gct ccc gaa cgc gtg ttc gag cct gac cct    144
Gly Arg Trp His Val Leu Ala Pro Glu Arg Val Phe Glu Pro Asp Pro
        35                  40                  45

```
atc gct gtc gag att ttg aag cgc tgt gat ggc gcg acg agt gtt gag      192
Ile Ala Val Glu Ile Leu Lys Arg Cys Asp Gly Ala Thr Ser Val Glu
 50                  55                  60 gaa atc gcc acc gca ctc gca aaa gag tac aat gca ccg ctg caa gag      240
Glu Ile Ala Thr Ala Leu Ala Lys Glu Tyr Asn Ala Pro Leu Gln Glu
 65                  70                  75                  80 atc ctc gcc gac acc ata tcc atg ttg cag gaa ctc tcg gac aag ggc      288
Ile Leu Ala Asp Thr Ile Ser Met Leu Gln Glu Leu Ser Asp Lys Gly
                 85                  90                  95 gtg gtc aaa gcc tag                                                   303
Val Val Lys Ala
            100

<210> SEQ ID NO 21
<211> LENGTH: 100
<212> TYPE: PRT
<213> ORGANISM: Hyphomicrobium denitrificans

<400> SEQUENCE: 21

Met Asn Ala Asp Ala Pro Arg Thr Arg Thr Met Val Val Pro Ala Ser
  1               5                  10                  15

Lys Pro Gly Leu Pro Thr His Ile Lys Leu Arg His Asp Ala Gly Arg
             20                  25                  30

Gly Arg Trp His Val Leu Ala Pro Glu Arg Val Phe Glu Pro Asp Pro
         35                  40                  45

Ile Ala Val Glu Ile Leu Lys Arg Cys Asp Gly Ala Thr Ser Val Glu
 50                  55                  60

Glu Ile Ala Thr Ala Leu Ala Lys Glu Tyr Asn Ala Pro Leu Gln Glu
 65                  70                  75                  80

Ile Leu Ala Asp Thr Ile Ser Met Leu Gln Glu Leu Ser Asp Lys Gly
                 85                  90                  95

Val Val Lys Ala
            100

<210> SEQ ID NO 22
<211> LENGTH: 1161
<212> TYPE: DNA
<213> ORGANISM: Hyphomicrobium denitrificans
<220> FEATURE:
<221> NAME/KEY: CDS
<222> LOCATION: (1)..(1161)

<400> SEQUENCE: 22 atg aac gaa atc gca ccg ttg gag cag ttt tcg cca gac cca gtg gcg       48
Met Asn Glu Ile Ala Pro Leu Glu Gln Phe Ser Pro Asp Pro Val Ala
  1               5                  10                  15 gaa gtc tgc gca cgc gcc ccg gtc ggc ctg ctc gcg gaa ctg acg cat       96
Glu Val Cys Ala Arg Ala Pro Val Gly Leu Leu Ala Glu Leu Thr His
             20                  25                  30 cgc tgc ccg ctt cag tgt cct tac tgc tcg aac ccg ctc gag ctt gac      144
Arg Cys Pro Leu Gln Cys Pro Tyr Cys Ser Asn Pro Leu Glu Leu Asp
         35                  40                  45 cgc gtc aac acg gaa ttg acg acg gcc gag tgg cag gac gtc atg cgt      192
Arg Val Asn Thr Glu Leu Thr Thr Ala Glu Trp Gln Asp Val Met Arg
 50                  55                  60 cag gca gcc gaa ctc ggc atc ctg cag atc cac ctt tcg ggt ggc gag      240
Gln Ala Ala Glu Leu Gly Ile Leu Gln Ile His Leu Ser Gly Gly Glu
 65                  70                  75                  80 ccg acg ctt cgc aag gat ctt gag gat atc gtc gat gtg gcg gcg aag      288
Pro Thr Leu Arg Lys Asp Leu Glu Asp Ile Val Asp Val Ala Ala Lys
```

-continued

```
                     85                  90                  95
gct ggc ctc tac acg aac ctc atc acg gcg ggc gtg acg ctg acc gaa      336
Ala Gly Leu Tyr Thr Asn Leu Ile Thr Ala Gly Val Thr Leu Thr Glu
            100                 105                 110 gat cgc ctg aag aag ctt cag gac ctg ggc ctc gac cac gtt cag ctg      384
Asp Arg Leu Lys Lys Leu Gln Asp Leu Gly Leu Asp His Val Gln Leu
            115                 120                 125 tcg atc cag gat gtc gac gac gcc aac gcc gag cgt atg tct gca tat      432
Ser Ile Gln Asp Val Asp Asp Ala Asn Ala Glu Arg Met Ser Ala Tyr
130                 135                 140 aaa ggc ggc ctc gcg aaa aag cgc gaa gtc ggc aag tgg gtg cgc aag      480
Lys Gly Gly Leu Ala Lys Lys Arg Glu Val Gly Lys Trp Val Arg Lys
145                 150                 155                 160 ctc ggc atg ccg ctc acc atc aat gcg ccg atc cat cgc ttc aat atc      528
Leu Gly Met Pro Leu Thr Ile Asn Ala Pro Ile His Arg Phe Asn Ile
                165                 170                 175 gag aac ctg ccg aac atc atc gac ttc gcg gtc gag atg ggc gcc ggt      576
Glu Asn Leu Pro Asn Ile Ile Asp Phe Ala Val Glu Met Gly Ala Gly
                180                 185                 190 cgc atc gag gtt gcg aac att cag tac tac gcc tgg gca ttg aag aac      624
Arg Ile Glu Val Ala Asn Ile Gln Tyr Tyr Ala Trp Ala Leu Lys Asn
            195                 200                 205 cgg gcg agc ctc atg ccg act cgc gcg caa gtc atc aag agc gcc gag      672
Arg Ala Ser Leu Met Pro Thr Arg Ala Gln Val Ile Lys Ser Ala Glu
            210                 215                 220 atc gtc gag gag gcc aag gaa cgc ctg aag ggc att ctc gtt ttc gac      720
Ile Val Glu Glu Ala Lys Glu Arg Leu Lys Gly Ile Leu Val Phe Asp
225                 230                 235                 240 ttc gtc gtt ccc gat tat tac gca aaa aca ccc aag ccg tgc atg ggc      768
Phe Val Val Pro Asp Tyr Tyr Ala Lys Thr Pro Lys Pro Cys Met Gly
                245                 250                 255 gga tgg ggc cgc ggc gtc atg aac gtc acc cca caa ggc aag gtg ctt      816
Gly Trp Gly Arg Gly Val Met Asn Val Thr Pro Gln Gly Lys Val Leu
                260                 265                 270 ccc tgc cac gcc tcc gaa acg att ccc gga ttg att ttc gat aac gtc      864
Pro Cys His Ala Ser Glu Thr Ile Pro Gly Leu Ile Phe Asp Asn Val
            275                 280                 285 aag gat cgg cgc ttg gcc gac atc tgg ctc aac ggg cag gca ttc cag      912
Lys Asp Arg Arg Leu Ala Asp Ile Trp Leu Asn Gly Gln Ala Phe Gln
            290                 295                 300 aag tat cgt ggt acg agc tgg atg aaa gag ccc tgc cgc agc tgc ccc      960
Lys Tyr Arg Gly Thr Ser Trp Met Lys Glu Pro Cys Arg Ser Cys Pro
305                 310                 315                 320 cgc gcc gaa atc gac ttt ggc ggc tgc cgc tgc cag gcg atg gcc ttc     1008
Arg Ala Glu Ile Asp Phe Gly Gly Cys Arg Cys Gln Ala Met Ala Phe
                325                 330                 335 acg ggc gac gcg gac aac acc gat ccg gcg tgc aag ttc tcg cca tat     1056
Thr Gly Asp Ala Asp Asn Thr Asp Pro Ala Cys Lys Phe Ser Pro Tyr
                340                 345                 350 cac gcc gct ttc gtg tca gcc gcc gag cag gag agc gcc gaa gcc gcg     1104
His Ala Ala Phe Val Ser Ala Ala Glu Gln Glu Ser Ala Glu Ala Ala
            355                 360                 365 ccc ccg ccc ttc gtc tac cgc cgc atg ggg ccg atc aag gct aca tcg     1152
Pro Pro Pro Phe Val Tyr Arg Arg Met Gly Pro Ile Lys Ala Thr Ser
370                 375                 380 gat aac tag                                                          1161
Asp Asn
385
```

<210> SEQ ID NO 23
<211> LENGTH: 386
<212> TYPE: PRT
<213> ORGANISM: Hyphomicrobium denitrificans

<400> SEQUENCE: 23

Met Asn Glu Ile Ala Pro Leu Glu Gln Phe Ser Pro Asp Pro Val Ala
1               5                   10                  15

Glu Val Cys Ala Arg Ala Pro Val Gly Leu Leu Ala Glu Leu Thr His
            20                  25                  30

Arg Cys Pro Leu Gln Cys Pro Tyr Cys Ser Asn Pro Leu Glu Leu Asp
        35                  40                  45

Arg Val Asn Thr Glu Leu Thr Thr Ala Glu Trp Gln Asp Val Met Arg
    50                  55                  60

Gln Ala Ala Glu Leu Gly Ile Leu Gln Ile His Leu Ser Gly Gly Glu
65                  70                  75                  80

Pro Thr Leu Arg Lys Asp Leu Glu Asp Ile Val Asp Val Ala Ala Lys
                85                  90                  95

Ala Gly Leu Tyr Thr Asn Leu Ile Thr Ala Gly Val Thr Leu Thr Glu
            100                 105                 110

Asp Arg Leu Lys Lys Leu Gln Asp Leu Gly Leu Asp His Val Gln Leu
        115                 120                 125

Ser Ile Gln Asp Val Asp Asp Ala Asn Ala Glu Arg Met Ser Ala Tyr
    130                 135                 140

Lys Gly Gly Leu Ala Lys Lys Arg Glu Val Gly Lys Trp Val Arg Lys
145                 150                 155                 160

Leu Gly Met Pro Leu Thr Ile Asn Ala Pro Ile His Arg Phe Asn Ile
                165                 170                 175

Glu Asn Leu Pro Asn Ile Ile Asp Phe Ala Val Glu Met Gly Ala Gly
            180                 185                 190

Arg Ile Glu Val Ala Asn Ile Gln Tyr Tyr Ala Trp Ala Leu Lys Asn
        195                 200                 205

Arg Ala Ser Leu Met Pro Thr Arg Ala Gln Val Ile Lys Ser Ala Glu
    210                 215                 220

Ile Val Glu Glu Ala Lys Glu Arg Leu Lys Gly Ile Leu Val Phe Asp
225                 230                 235                 240

Phe Val Val Pro Asp Tyr Tyr Ala Lys Thr Pro Lys Pro Cys Met Gly
                245                 250                 255

Gly Trp Gly Arg Gly Val Met Asn Val Thr Pro Gln Gly Lys Val Leu
            260                 265                 270

Pro Cys His Ala Ser Glu Thr Ile Pro Gly Leu Ile Phe Asp Asn Val
        275                 280                 285

Lys Asp Arg Arg Leu Ala Asp Ile Trp Leu Asn Gly Gln Ala Phe Gln
    290                 295                 300

Lys Tyr Arg Gly Thr Ser Trp Met Lys Glu Pro Cys Arg Ser Cys Pro
305                 310                 315                 320

Arg Ala Glu Ile Asp Phe Gly Gly Cys Arg Cys Gln Ala Met Ala Phe
                325                 330                 335

Thr Gly Asp Ala Asp Asn Thr Asp Pro Ala Cys Lys Phe Ser Pro Tyr
            340                 345                 350

His Ala Ala Phe Val Ser Ala Ala Glu Gln Glu Ser Ala Glu Ala Ala
        355                 360                 365

Pro Pro Pro Phe Val Tyr Arg Arg Met Gly Pro Ile Lys Ala Thr Ser
    370                 375                 380

Asp Asn
385

<210> SEQ ID NO 24
<211> LENGTH: 3476
<212> TYPE: DNA
<213> ORGANISM: Hyphomicrobium denitrificans

<400> SEQUENCE: 24

| | | | | | |
|---|---|---|---|---|---|
| atggaaagca | gttaccgctt | tggaggaacc | acaatgaaaa | tctggacgaa | gcccgctgtg    60 |
| cgcgagcagg | aagttggtct | cgaagtgacg | agctacctgc | cggctgaaat | cgacctcatc   120 |
| tgaggattga | tttcttcggt | ctcacaacac | tggtgagata | acggcgcggc | ggtcggtgcg   180 |
| gttcatcggc | cgccgcagtc | atatccttgc | aaattttct  | gcgcagcctc | ttcggcgaga   240 |
| tggcgggcgc | aagacaccgg | tatccatgat | cataaaagtg | ctcgggtcct | ccgctggggg   300 |
| tggattcccg | cagtggaact | gcaatggcat | gcagtcggca | aaggttcgct | caggcgctgc   360 |
| cgggtttaag | gcgcgcttgc | aatcgtccct | tgccgcttcg | agcgacggca | agaattgggt   420 |
| gttgctcaac | gcctcgcccg | acattcgcca | gcagatcaac | gagacgcccg | agttgcaccc   480 |
| tgaaacgacg | ggcgcaaagc | gtaattcgcc | gatcaaggcc | gttgtcgtca | ccaatgccga   540 |
| cgtcgatcac | atcatcggac | tgatcggcct | ccgcgaaggt | cagccgtttt | cgatctacgg   600 |
| ttccgacctc | gtcctcgcga | cgctgaaggc | aaattcagtt | tcaacgtct  | gcaaccccga   660 |
| gatcgtaccg | cgcttggaac | tgcccttcga | caggccgacc | gaactgcatg | cgccggcgt    720 |
| cgacctcgga | ctgacggtcg | aagccttccc | tgtcccaggc | aaggttgcgc | tctttctgga   780 |
| aagggcggc  | gccaacgaaa | attacggcag | ccgcgacggc | gacaccatcg | gcttgaaagt   840 |
| gacggatcgt | aaagccggca | agtcgttttt | ctacattccc | ggctgcgccg | aagtcgacgc   900 |
| gccgctcgcc | gatcgcatcc | gcggagccga | tgtcattttc | ttcgacggca | cgctttacga   960 |
| agacggcgaa | atgatcgctc | aaggattgtt | gaacaagacc | ggcaagcgaa | tgggccatat  1020 |
| ttcggtctcc | ggtcacgaag | gctctatcgc | ggctttgagc | catctcaacg | ttcgccgaaa  1080 |
| aattacgtt  | cacatcaaca | attcaaaccc | gatcctggat | gaaaattcgg | aagctcgaaa  1140 |
| agctgttgaa | acagccgggt | gggaggttgg | ttttgatgga | atggaggtcc | gcttatgaac  1200 |
| ccggtcagcg | ttggaaagaa | attagcagag | cttcgcggtg | acgaggcgcc | gatgccggtc  1260 |
| gccgaattcg | aagcagccat | tcgtgcggtc | ggacccgagc | gctaccatga | cctgcatccc  1320 |
| ttccatcaca | tgcttcacgg | cggcaagctg | aacaagggac | aggtgcaggc | ctgggcgctc  1380 |
| aatcgcttct | gctatcagtc | cgccgttccg | cgcaaggatg | cagcgctcat | cagcggggtt  1440 |
| tacgatcgcg | agcttcgccg | cgagtggacg | catcgcattc | tcgatcatga | tggtctgctt  1500 |
| cctgatgaag | aaggcggcat | cgagcgttgg | ctcgtgctga | cggacggcct | tggactcgat  1560 |
| cgcgagtacg | tcatctcgcg | gcgcggcgcg | cttccggcga | ccgtctttgc | cgtcgaggct  1620 |
| tacgtcacgt | tcgtgcgcga | gcagccattg | acgatcgccg | tcgcctcctc | gctgaccgag  1680 |
| ctgttcgcgc | cgaagattca | caagaacgc  | atcgccggca | tgctcgagaa | ctacaacttc  1740 |
| atcgacgaca | aggtgatggc | gtatttcaaa | cgccgcctga | cgcaggctcc | gcgcgacgcc  1800 |
| gatttcgcac | tgaactacat | actcgagaac | gcccgcacgc | gcgacgaaca | gcaagcctgc  1860 |
| atcgacgcgg | tgcgcttcaa | atgcaatgtt | ctctgggtgc | agctcgacgc | gctctaccac  1920 |
| gcttacgtcg | acgacacat  | tcctccggga | gctttccggc | cggagaatta | acgaggctta  1980 |
| cgtatgaacg | cagacgcacc | gcgtacgaga | acgatggtcg | tcccggcttc | caagcccgga  2040 |

```
ctgccgacgc acatcaagct gcgccacgac gccggccgcg gccgatggca cgtgcttgct    2100
cccgaacgcg tgttcgagcc tgaccctatc gctgtcgaga ttttgaagcg ctgtgatggc    2160
gcgacgagtg ttgaggaaat cgccaccgca ctcgcaaaag agtacaatgc accgctgcaa    2220
gagatcctcg ccgacaccat atccatgttg caggaactct cggacaaggg cgtggtcaaa    2280
gcctaggacg cgtgaaacag aacggagccg atgtcatgaa cgaaatcgca ccgttggagc    2340
agttttcgcc agacccagtg gcggaagtct cgcgcacgcg cccggtcggc ctgctcgcgg    2400
aactgacgca tcgctgcccg cttcagtgtc cttactgctc gaacccgctc gagcttgacc    2460
gcgtcaacac ggaattgacg acggccgagt ggcaggacgt catgcgtcag gcagccgaac    2520
tcggcatcct gcagatccac ctttcgggtg gcgagccgac gcttcgcaag atcttgagg    2580 atatcgtcga tgtggcggcg aaggctggcc tctacacgaa cctcatcacg gcgggcgtga    2640
cgctgaccga agatcgcctg aagaagcttc aggacctggg cctcgaccac gttcagctgt    2700
cgatccagga tgtcgacgac gccaacgccg agcgtatgtc tgcatataaa ggcggcctcg    2760
cgaaaaagcg cgaagtcggc aagtgggtgc gcaagctcgg catgccgctc accatcaatg    2820
cgccgatcca tcgcttcaat atcgagaacc tgccgaacat catcgacttc gcggtcgaga    2880
tgggcgccgg tcgcatcgag gttgcgaaca ttcagtacta cgcctgggca ttgaagaacc    2940
gggcgagcct catgccgact cgcgcgcaag tcatcaagag cgccgagatc gtcgaggagg    3000
ccaaggaacg cctgaagggc attctcgttt tcgacttcgt cgttcccgat tattacgcaa    3060
aaacacccaa gccgtgcatg ggcggatggg gccgcggcgt catgaacgtc accccacaag    3120
gcaaggtgct tccctgccac gcctccgaaa cgattcccgg attgattttc gataacgtca    3180
aggatcggcg cttggccgac atctggctca cgggcaggc attccagaag tatcgtggta    3240
cgagctggat gaaagagccc tgccgcagct gccccgcgc cgaaatcgac tttggcggct    3300
gccgctgcca ggcgatggcc ttcacgggcg acgcggacaa caccgatccg gcgtgcaagt    3360
tctcgccata tcacgccgct ttcgtgtcag ccgccgagca ggagagcgcc gaagccgcgc    3420
ccccgccctt cgtctaccgc cgcatggggc cgatcaaggc tacatcggat aactag         3476
```

<210> SEQ ID NO 25
<211> LENGTH: 108
<212> TYPE: DNA
<213> ORGANISM: Hyphomicrobium denitrificans
<220> FEATURE:
<221> NAME/KEY: CDS
<222> LOCATION: (1)..(108)

<400> SEQUENCE: 25

```
atg caa gag agc ctg ctt aag gag ccg gaa gca aag aca tgg gtc gcg        48
Met Gln Glu Ser Leu Leu Lys Glu Pro Glu Ala Lys Thr Trp Val Ala
1               5                   10                  15 cct gcg tac tgc gac ctg cgt ctc gga ttc gaa gtc acg gcc tac atc        96
Pro Ala Tyr Cys Asp Leu Arg Leu Gly Phe Glu Val Thr Ala Tyr Ile
            20                  25                  30 tac gtt cgg tag                                                       108
Tyr Val Arg
        35
```

<210> SEQ ID NO 26
<211> LENGTH: 35
<212> TYPE: PRT
<213> ORGANISM: Hyphomicrobium denitrificans

<400> SEQUENCE: 26

```
Met Gln Glu Ser Leu Leu Lys Glu Pro Glu Ala Lys Thr Trp Val Ala
1               5                   10                  15

Pro Ala Tyr Cys Asp Leu Arg Leu Gly Phe Glu Val Thr Ala Tyr Ile
            20                  25                  30

Tyr Val Arg
        35

<210> SEQ ID NO 27
<211> LENGTH: 102
<212> TYPE: DNA
<213> ORGANISM: Hyphomicrobium denitrificans
<220> FEATURE:
<221> NAME/KEY: CDS
<222> LOCATION: (1)..(102)

<400> SEQUENCE: 27 atg gag gac atc atg aag acc tgg aca aag cct gcc gtt cgc gag cag      48
Met Glu Asp Ile Met Lys Thr Trp Thr Lys Pro Ala Val Arg Glu Gln
1               5                   10                  15 gaa gtc ggc ctc gaa gtt acc tcg tac ctt ccg gcc gag atc gac ctc      96
Glu Val Gly Leu Glu Val Thr Ser Tyr Leu Pro Ala Glu Ile Asp Leu
            20                  25                  30 atc taa                                                             102
Ile

<210> SEQ ID NO 28
<211> LENGTH: 33
<212> TYPE: PRT
<213> ORGANISM: Hyphomicrobium denitrificans

<400> SEQUENCE: 28

Met Glu Asp Ile Met Lys Thr Trp Thr Lys Pro Ala Val Arg Glu Gln
1               5                   10                  15

Glu Val Gly Leu Glu Val Thr Ser Tyr Leu Pro Ala Glu Ile Asp Leu
            20                  25                  30

Ile

<210> SEQ ID NO 29
<211> LENGTH: 20
<212> TYPE: DNA
<213> ORGANISM: Artificial sequence
<220> FEATURE:
<223> OTHER INFORMATION: primer EG539

<400> SEQUENCE: 29
tcgccgagct cgaaatgctg                                                20

<210> SEQ ID NO 30
<211> LENGTH: 29
<212> TYPE: DNA
<213> ORGANISM: Artificial sequence
<220> FEATURE:
<223> OTHER INFORMATION: primer EG540

<400> SEQUENCE: 30
atactgcagc gacgccttct tagttgaag                                      29

<210> SEQ ID NO 31
<211> LENGTH: 20
<212> TYPE: DNA
<213> ORGANISM: Artificial sequence
<220> FEATURE:
<223> OTHER INFORMATION: primer EG568
```

-continued

<400> SEQUENCE: 31
aatctatgcc gtgtcgcatc					20

<210> SEQ ID NO 32
<211> LENGTH: 30
<212> TYPE: DNA
<213> ORGANISM: Artificial sequence
<220> FEATURE:
<223> OTHER INFORMATION: primer EG569

<400> SEQUENCE: 32
atatctagac gtcaaattcg gagatgatcg					30

<210> SEQ ID NO 33
<211> LENGTH: 30
<212> TYPE: DNA
<213> ORGANISM: Artificial sequence
<220> FEATURE:
<223> OTHER INFORMATION: primer EG570

<400> SEQUENCE: 33
atatctagat gatcgacaaa tcgttgcagc					30

<210> SEQ ID NO 34
<211> LENGTH: 28
<212> TYPE: DNA
<213> ORGANISM: Artificial sequence
<220> FEATURE:
<223> OTHER INFORMATION: primer EG571

<400> SEQUENCE: 34
ataggatcca ctgcgctacc gaacgtag					28

<210> SEQ ID NO 35
<211> LENGTH: 28
<212> TYPE: DNA
<213> ORGANISM: Artificial sequence
<220> FEATURE:
<223> OTHER INFORMATION: primer EG572

<400> SEQUENCE: 35
ataggatcca cacgcagacg tgatagac					28

<210> SEQ ID NO 36
<211> LENGTH: 29
<212> TYPE: DNA
<213> ORGANISM: Artificial sequence
<220> FEATURE:
<223> OTHER INFORMATION: primer EG573

<400> SEQUENCE: 36
atagagctcg gaagcgatta attgcttgc					29

<210> SEQ ID NO 37
<211> LENGTH: 23
<212> TYPE: PRT
<213> ORGANISM: Pseudomonas fluorescens

<400> SEQUENCE: 37

Met Trp His Lys Pro Ala Tyr Thr Asp Leu Arg Ile Gly Phe Glu Val
1               5                   10                  15

Thr Met Tyr Phe Ala Asn Arg
            20

<210> SEQ ID NO 38
<211> LENGTH: 24
<212> TYPE: PRT
<213> ORGANISM: Pseudomonas fluorescens

<400> SEQUENCE: 38

Met Thr Trp Ser Lys Pro Ala Tyr Thr Asp Leu Arg Ile Gly Phe Glu
1               5                   10                  15

Val Thr Met Tyr Phe Ala Ser Arg
            20

<210> SEQ ID NO 39
<211> LENGTH: 24
<212> TYPE: PRT
<213> ORGANISM: Ralstonia pickettii

<400> SEQUENCE: 39

Met Ala Trp Gln Lys Pro Glu Ala Thr Asp Leu Arg Phe Gly Phe Glu
1               5                   10                  15

Ile Thr Met Tyr Ile Ala Asn Arg
            20

<210> SEQ ID NO 40
<211> LENGTH: 24
<212> TYPE: PRT
<213> ORGANISM: Ralstonia pickettii

<400> SEQUENCE: 40

Met Asn Trp Thr Thr Pro Ala Tyr Thr Glu Leu Arg Leu Gly Phe Glu
1               5                   10                  15

Ile Thr Met Tyr Ile Ala Asn Arg
            20

<210> SEQ ID NO 41
<211> LENGTH: 23
<212> TYPE: PRT
<213> ORGANISM: Methylotenera mobilis

<400> SEQUENCE: 41

Met Trp Thr Thr Pro Ala Ala Thr Glu Met Arg Phe Gly Phe Glu Val
1               5                   10                  15

Thr Met Tyr Val Met Asn Lys
            20

<210> SEQ ID NO 42
<211> LENGTH: 26
<212> TYPE: PRT
<213> ORGANISM: Bradyrhizobium sp.

<400> SEQUENCE: 42

Met Ala Trp Lys Ala Pro Lys Ile Val Glu Val Pro Val Gly Met Glu
1               5                   10                  15

Ile Asn Met Tyr Ala Cys Ala Ala Arg Lys
            20                  25

<210> SEQ ID NO 43
<211> LENGTH: 26
<212> TYPE: PRT
<213> ORGANISM: Bradyrhizobium sp.

<400> SEQUENCE: 43

Met Ala Trp Lys Thr Pro Lys Ile Val Glu Val Pro Val Gly Met Glu
1               5                   10                  15

```
Ile Asn Met Tyr Ala Cys Ala Ala Arg Lys
            20                  25

<210> SEQ ID NO 44
<211> LENGTH: 31
<212> TYPE: PRT
<213> ORGANISM: Bradyrhizobium sp.

<400> SEQUENCE: 44

Met Ser Trp Thr Ala Pro Lys Ile Val Glu Val Pro Val Gly Met Glu
1               5                   10                  15

Ile Asn Met Tyr Ala Cys Ala Ser Arg Lys Ala Glu Arg Arg Ser
            20                  25                  30

<210> SEQ ID NO 45
<211> LENGTH: 24
<212> TYPE: PRT
<213> ORGANISM: Methylococcus capsulatus

<400> SEQUENCE: 45

Met Arg Trp Glu Lys Pro Ser Tyr Asn Asp Met Arg Phe Gly Phe Glu
1               5                   10                  15

Val Thr Met Tyr Ile Tyr Asn Arg
            20

<210> SEQ ID NO 46
<211> LENGTH: 23
<212> TYPE: PRT
<213> ORGANISM: Colwellia psychrerythraea

<400> SEQUENCE: 46

Met Trp Thr Lys Pro Lys Phe Glu Glu Met Arg Leu Gly Phe Glu Val
1               5                   10                  15

Thr Leu Tyr Ile Ser Asn Arg
            20

<210> SEQ ID NO 47
<211> LENGTH: 26
<212> TYPE: PRT
<213> ORGANISM: Gluconobacter oxydans

<400> SEQUENCE: 47

Met Ala Trp Asn Thr Pro Lys Val Thr Glu Ile Pro Leu Gly Ala Glu
1               5                   10                  15

Ile Asn Ser Tyr Val Cys Gly Glu Lys Lys
            20                  25

<210> SEQ ID NO 48
<211> LENGTH: 52
<212> TYPE: PRT
<213> ORGANISM: Methylobacillus flagellatus

<400> SEQUENCE: 48

Met Ser Lys Leu Gly Leu Tyr Asp Gly Asn His Gly Leu Arg Gly Thr
1               5                   10                  15

Asp Cys Ala Ala Ser Thr His Leu Lys Arg Arg Leu Ile Met Trp Thr
            20                  25                  30

Lys Pro Glu Val Thr Glu Met Arg Phe Gly Phe Glu Val Thr Met Tyr
                35                  40                  45

Val Cys Asn Arg
    50
```

<210> SEQ ID NO 49
<211> LENGTH: 32
<212> TYPE: PRT
<213> ORGANISM: Dinoroseobacter shibae

<400> SEQUENCE: 49

Met Ala Trp Thr Lys Pro Ile Ile Arg Glu Ile Glu Cys Gly Met Glu
1               5                   10                  15

Ile Asn Met Tyr Gly Pro Asp Ser Asp Glu Gly Arg Glu Val Leu Phe
            20                  25                  30

<210> SEQ ID NO 50
<211> LENGTH: 24
<212> TYPE: PRT
<213> ORGANISM: Erwinia amylovora

<400> SEQUENCE: 50

Met Gln Trp Thr Lys Pro Thr Phe Ile Asp Met Arg Leu Gly Leu Glu
1               5                   10                  15

Val Thr Leu Tyr Ile Ser Asn Arg
            20

<210> SEQ ID NO 51
<211> LENGTH: 60
<212> TYPE: PRT
<213> ORGANISM: Leptothrix discophora

<400> SEQUENCE: 51

Met Val Leu Ala Met Thr Pro Arg Ala Pro Ala Pro Thr Leu His Pro
1               5                   10                  15

His Gln His Thr Leu Leu Ala Ser Leu Thr Arg Thr Ala Asn Pro Ile
            20                  25                  30

Glu Gly Asp Leu Met Thr Trp Thr Thr Pro Ala Ala Cys Asp Phe Arg
        35                  40                  45

Phe Gly Phe Glu Ile Thr Met Tyr Ile Ala Ala Arg
    50                  55                  60

<210> SEQ ID NO 52
<211> LENGTH: 5
<212> TYPE: PRT
<213> ORGANISM: Artificial Sequence
<220> FEATURE:
<223> OTHER INFORMATION: conserved sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 52

Glu Xaa Xaa Xaa Tyr
1               5